(12) United States Patent
Herron et al.

(10) Patent No.: US 6,356,676 B1
(45) Date of Patent: Mar. 12, 2002

(54) LENS AND ASSOCIATABLE FLOW CELL

(75) Inventors: James N. Herron; Douglas A. Christensen; Victor A. Pollak, all of Salt Lake City, UT (US); Richard D. McEachern, Ann Arbor, MI (US); Eric M. Simon, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/608,714

(22) Filed: Jun. 30, 2000

Related U.S. Application Data

(62) Division of application No. 09/142,948, filed as application No. PCT/US97/04398 on Mar. 19, 1997, now Pat. No. 6,108,463

(60) Provisional application No. 60/022,434, filed on Aug. 8, 1996, and provisional application No. 60/013,195, filed on Mar. 19, 1996.

(51) Int. Cl.⁷ ................................................. G02B 6/26
(52) U.S. Cl. ............................ 385/12; 385/15; 385/33; 385/37; 385/130; 385/146; 422/82.11
(58) Field of Search ............................ 385/146, 12, 15, 385/33, 37, 130; 422/82.11

(56) References Cited

U.S. PATENT DOCUMENTS

| | | | |
|---|---|---|---|
| 3,308,709 A | * | 3/1967 | Harrick |
| 3,490,847 A | | 1/1970 | Berz et al. |
| 3,535,016 A | * | 10/1970 | Malifaud |
| 4,746,179 A | | 5/1988 | Dahne et al. |
| 4,818,710 A | | 4/1989 | Sutherland et al. |
| 4,980,278 A | | 12/1990 | Yamada et al. |
| 5,064,619 A | | 11/1991 | Finlan |
| 5,202,950 A | | 4/1993 | Arego et al. |
| 5,485,277 A | | 1/1996 | Foster |
| 5,512,492 A | | 4/1996 | Herron et al. |

FOREIGN PATENT DOCUMENTS

| | | |
|---|---|---|
| DE | 44 12 893 A1 | 10/1995 |
| EP | 0 185 126 A | 6/1986 |
| WO | WO 94/27137 | 11/1994 |
| WO | WO 95/03538 | 2/1995 |

OTHER PUBLICATIONS

Supplementary European Search Report, EP 97 91 6086, dated Jan. 31, 2000.

* cited by examiner

Primary Examiner—Hung N. Ngo
(74) Attorney, Agent, or Firm—TraskBritt

(57) ABSTRACT

Improvements in a biosensor of the type having reservoirs or wells for analyzing a biological liquid are disclosed. A biosensor includes a waveguide placed between a plurality of members such as plates at least one of the members being formed to define the walls of the reservoirs where the liquid is biologically analyzed. The walls of the reservoirs are made of an inert, opaque material such as a metal. Although the biosensor may include a gasket, the gasket is associated with the members and waveguide in such a way (e.g., by recessing the gasket into a channel formed into a metal plate) so that the gasket does not form any significant portion of the reservoir wall. Waveguides of varying composition (e.g., plastic, quartz or glass) may be associated with the members to form the biosensor. The metal plate of the biosensor has input and output ports for infusing, draining, or oscillating the liquid to be analyzed in the reaction reservoir. Also disclosed is a sled-shaped waveguide associated with a rear lens to couple light out of the waveguide to serve as a quality control measure thus insuring that the biosensor is properly placed and that the light is working.

15 Claims, 13 Drawing Sheets

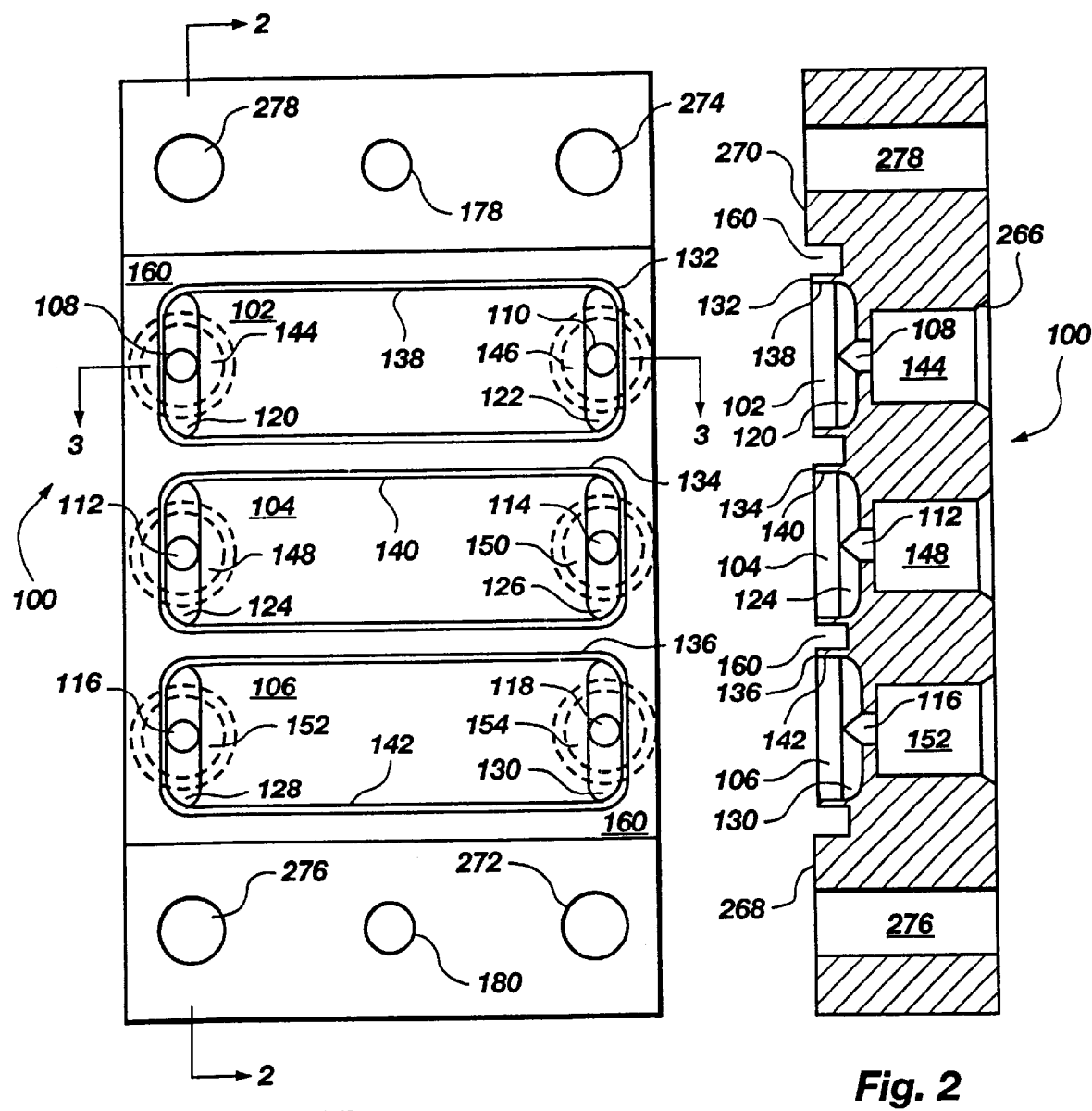
Fig. 1
Fig. 2
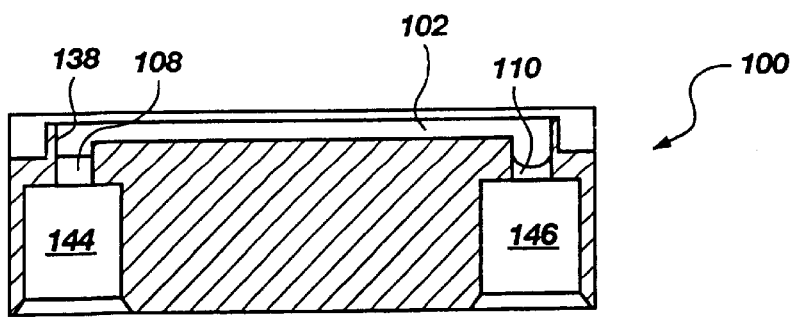
Fig. 3

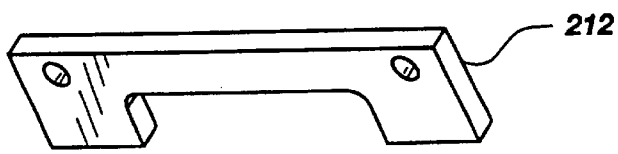
Fig. 14
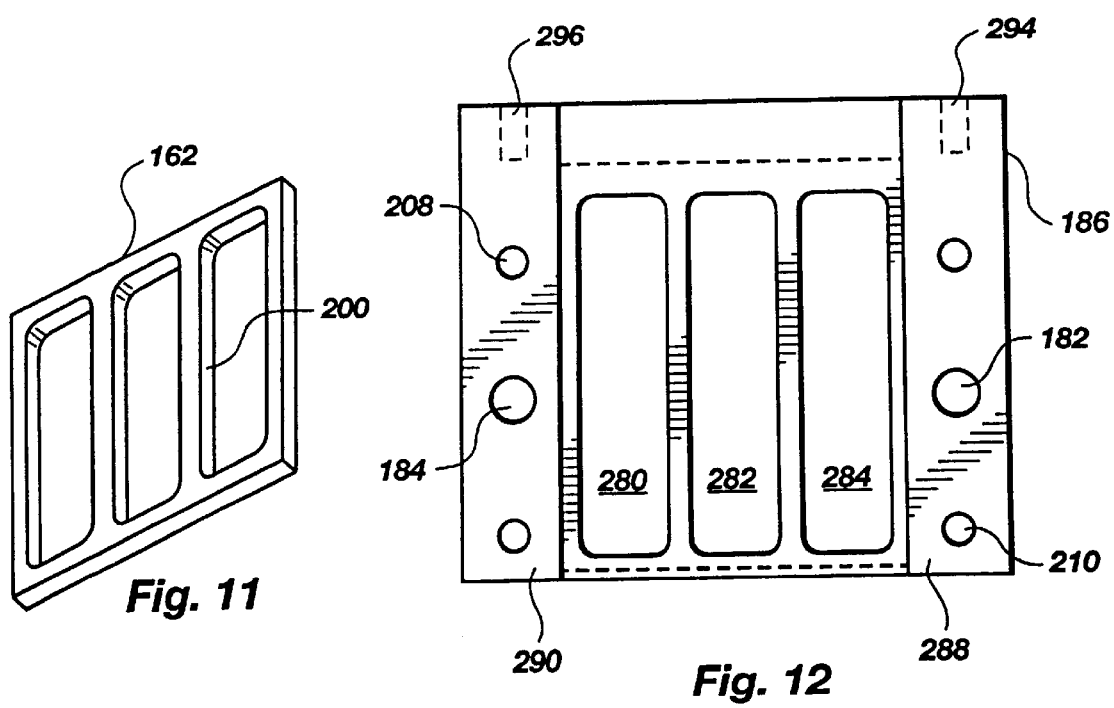
Fig. 11
Fig. 12
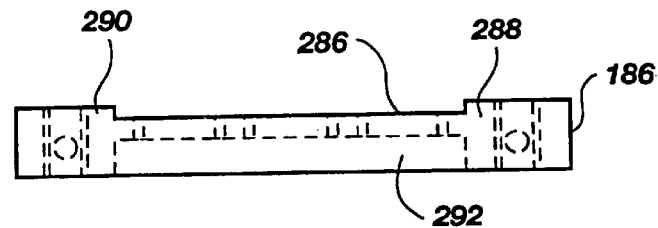
Fig. 13

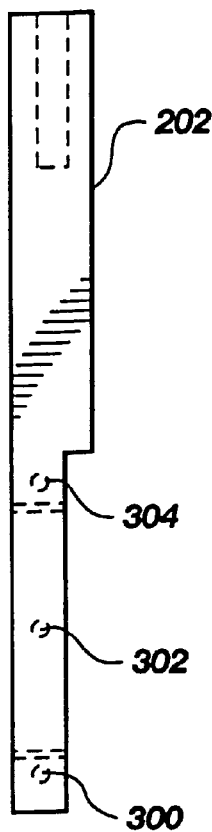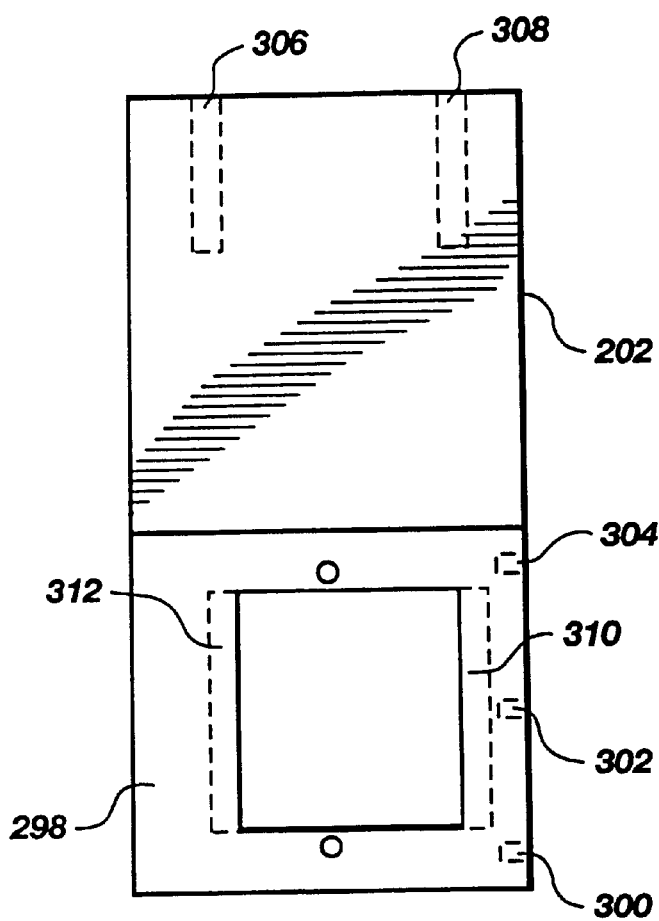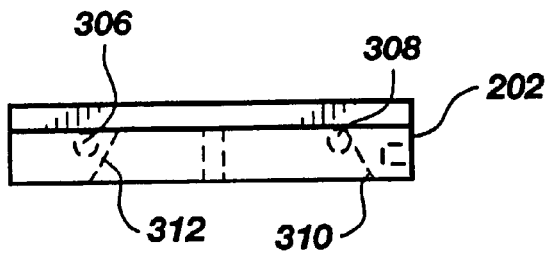
Fig. 16
Fig. 15
Fig. 17

US 6,356,676 B1

LENS AND ASSOCIATABLE FLOW CELL

CROSS-REFERENCE TO RELATED APPLICATIONS

This patent application is a divisional of application Ser. No. 09/142,948, filed Sep. 18, 1998, now U.S. Pat. No. 6,108,463, which is an application under 35 U.S.C. §371 of PCT/US 97/04398 filed on Mar. 19, 1997 claiming priority from U.S. Provisional Patent Application No. 60/022,434 filed on Aug. 8, 1996 and U.S. Provisional Patent Application No. 60/013,195 filed on Mar. 19, 1996.

TECHNICAL FIELD

This invention relates generally to components of a diagnostic apparatus, and more particularly to an improved biosensor having a lens ("waveguide") and associated flow cell.

BACKGROUND ART

International Application No. PCT/US94/05567 (International Publication No. 94/27137, published Nov. 24, 1994) to the University of Utah Research Foundation discloses an apparatus for multi-analyte homogeneous fluoroimmunoassays. In one embodiment, the application discloses an apparatus which uses a biosensor having a planar waveguide sandwiched, with an associated gasket, between two plates (FIGS. 3A–3C of Internat'l Publ. No. 94/27137). The inner edges of the gaskets serve as walls for a reaction reservoir or well. Fluorescence-emitting tracer molecules are bound to the waveguide surface and are excited by an evanescent field penetrating into the adjacent solution from a light beam propagated within the waveguide, the beam being introduced at, for example, a front end of the waveguide. In the reaction reservoir, a liquid (e.g., serum or blood) is introduced and is allowed to admix with capture molecules associated with the waveguide surface (e.g., by "coating chemistry" as disclosed on pages 32 to 33 of the international application). The emitted fluorescence is then directly collected from the zone of evanescent penetration. In one particular embodiment, the biosensor has transparent walls which define the reservoirs. (E.g., FIGS. 11A–C of Internatl. Publn. No. 94/27137). The application also discloses integrally formed or molded biosensors. (E.g., FIGS. 12A, 12B & 13 of Internatl. Publn. No. 94/27137).

Unfortunately, the waveguide portion of integrally formed or molded biosensors may exhibit deformation upon fabrication, or warping during storage or temperature changes. Also, gaskets may not reliably seal or are not always sufficiently inert to reactants, and thus may interfere with the desired analysis.

It would be desirable to have a biosensor having reservoirs with inert walls, the walls being readily detachable from the waveguide so that one waveguide could be readily exchanged for another.

DISCLOSURE OF THE INVENTION

The invention includes a biosensor with a reservoir or reservoirs, the biosensor including a waveguide placed (e.g., "sandwiched") between a plurality of members such as plates, at least one of the members being formed to define the walls of the reservoir or reservoirs where the reaction to be analyzed takes place. The reservoir walls are preferably an inert, opaque material such as a passivated metal (e.g., black anodized aluminum). Although the biosensor may include a gasket, the gasket is associated with the plurality of members and waveguide in such a way (e.g., by recessing the gasket into a channel formed into a metal plate) so that the gasket does not form any significant portion of the reservoir wall. Waveguides of varying composition (e.g., plastic, quartz, glass or siliconoxynitride) may be associated with the members to form the biosensor. A lens or lenses may be integrated with the waveguide. The metal plate of the biosensor has input and output ports for infusing, draining, or oscillating the liquid to be analyzed in the reaction reservoir.

Due to the sandwiching of the waveguide in between the members, the planar waveguide is generally less distorted than that of an integrally formed biosensor. A reaction to be analyzed is not interfered with due to the use of opaque, inert metal to structurally define the reservoir.

The biosensor design is advantageously configured to interact with a flat waveguide having a rear integrated lens design for reading light passing through the waveguide (not fluorescent/evanescent light, but reading the core laser beam light) to monitor coupling efficiency and beam quality. The invention thus also includes a flat waveguide associated with a rear lens to couple light out of the waveguide (and a biosensor using such a lens) to serve as a quality control measure, thus insuring that the biosensor is properly placed and that the light source is working.

The invention also includes orienting the biosensor in a particular position relative to an optical reading device and laser which increases the performance of the biosensor to the point where, surprisingly, whole blood can be quickly analyzed.

BRIEF DESCRIPTION OF THE DRAWINGS

In the drawings, which depict presently preferred embodiments of the invention and in which like reference numerals refer to like parts in different views:

FIG. 1 depicts an enlarged bottom view of the flow cell top which may be used with the invention.

FIG. 2 depicts an enlarged section view of the flow cell top of the preceding figure along section line 2—2.

FIG. 3 depicts an enlarged section view of the flow cell top of FIG. 1 along section line 3—3.

FIG. 11 depicts an enlarged perspective view of a gasket for use with the invention.

FIG. 12 depicts an enlarged top view of a second frame member ("flow cell bottom") for association with the flow cell top of FIGS. 1 through 3.

FIG. 13 depicts an enlarged side view of the second frame member of the preceding figure.

FIG. 14 depicts an enlarged perspective view of the registration plate forming part of the flow cell assembly of FIG. 4.

FIG. 15 depicts an enlarged top view of the stage member of the flow cell assembly of FIG. 4.

FIG. 16 depicts an enlarged side view of the stage member of the preceding figure.

FIG. 17 depicts an enlarged view of the preceding two figures.

DETAILED DESCRIPTION OF THE INVENTION

A. Flow Cell

The flow cell top, generally 100, depicted in FIGS. 1 through 3 is preferably made of a light absorbing material (e.g., a metal such as aluminum having a passivated surface such as black anodized surface). The depicted flow cell top 100 is generally plate-like, and is formed to contain a plurality of wells or reservoirs 102, 104, 106 (for example, two to ten reservoirs).

A design with at least two individual reservoirs has significant advantages over a single reservoir embodiment for instances when it is desirable to measure the test sample fluorescence simultaneously with fluorescence from a "control" region on the same waveguide. For example, the level of non-specific binding to the waveguide (or non-specific fluorescence) can be subtracted from the test sample fluorescence. Also, measurement changes due to fluctuations in intensity of the exciting light can be corrected. In a displacement assay, the "control" region could be a pre-loaded waveguide with no analyte present in the sample, or with a known amount of analyte. With the depicted embodiment of three or more wells, fluorescence can be measured for both a no-analyte control and at least one known calibration analyte sample in addition to the "unknown" or test sample. Although, even with a single reservoir, the invention is able to analyze multiple analytes in a single sample (e.g., by use of a single waveguide in multiple experiments).

Figure 23:
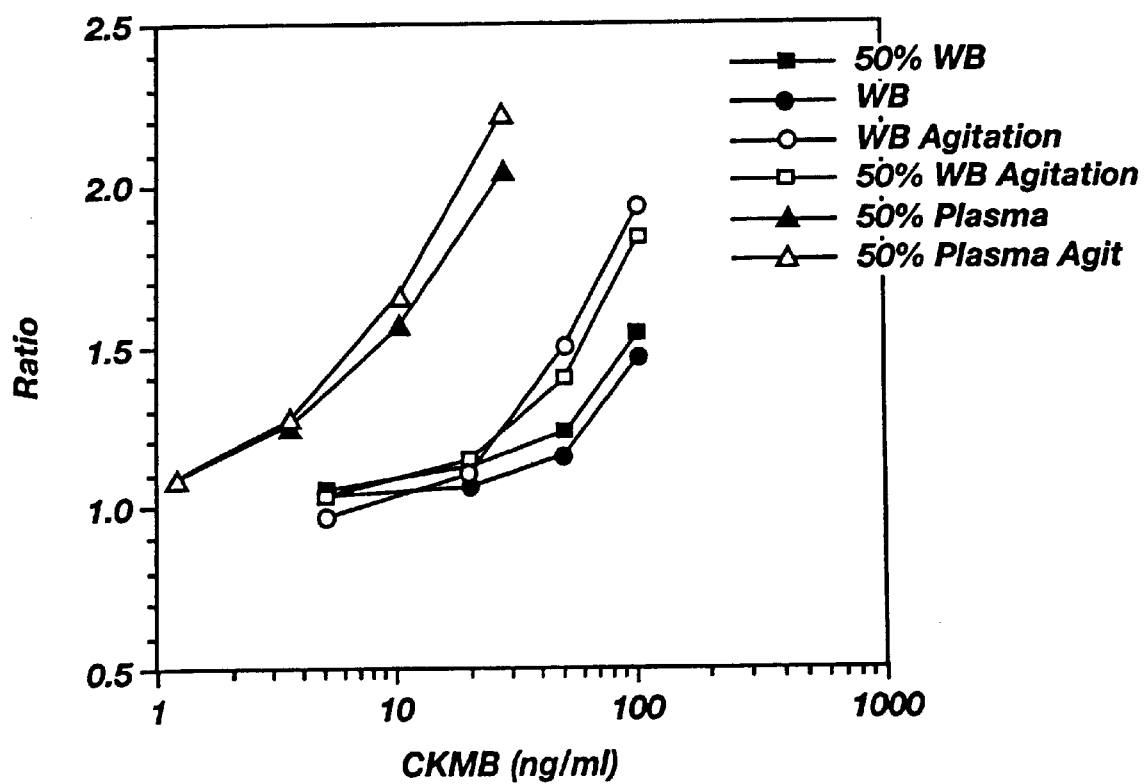
FIG. 23 is a graph depicting the effect of agitation (oscillation) on a CK-MB assay on whole blood ("WB"), 50% WB, and 50% plasma using a device according to the invention (dilution with outdated CPDA anticoagulant solution).

In the depicted embodiment, the reservoirs 102–106 have respective inlet/outlet apertures 108, 110, 112, 114, 116, 118 extending through the flow cell top 100 for injecting and withdrawing the liquid to be analyzed into the reservoirs 102–106. In some cases, this liquid may be oscillated into and out of the reservoir with a pump, which enhances the mixing of the analyte and reactant (see, e.g., FIG. 23). With oscillation, the performance (e.g., speed) of the assay is increased. In the depicted embodiment, each port 108–118 is associated with its own depressed recess formed 120, 122, 124, 126, 128, 130 in the flow cell top 100.

Between the recesses associated with a particular reservoir, lateral or longitudinal channels may be formed in the flow cell top to aid in mixing the liquid contained within the reservoir (not shown).

The outer periphery of the reservoirs 102–106 are each defined by respective walls 132, 134, 136 which are preferably integrally formed with the rest of the flow cell top 100, although they may be a separate component of the flow cell top. The inner circumferences 138, 140, 142 of the walls 132–136 are made of an inert, opaque material such as an inert, opaque plastic, or a metal such as passivated, black anodized aluminum, copper, stainless steel, or similar alloy. In the depicted embodiment, the entire flow cell top 100 is made of a metal, while in other embodiments (not shown), the flow cell may be made of a non-metallic material, and an opaque, dark material or metal sleeve placed within the reservoirs (not shown). Material in contact with the liquid should exhibit low protein absorption properties. Accordingly, a metal, a hydrophilic non-metallic material or a hydrophobic non-metallic material coated with a thin film of hydrophilic material (e.g., PEG™, PLURONICS™ or other hydrogels) may be used.

Figure 4:
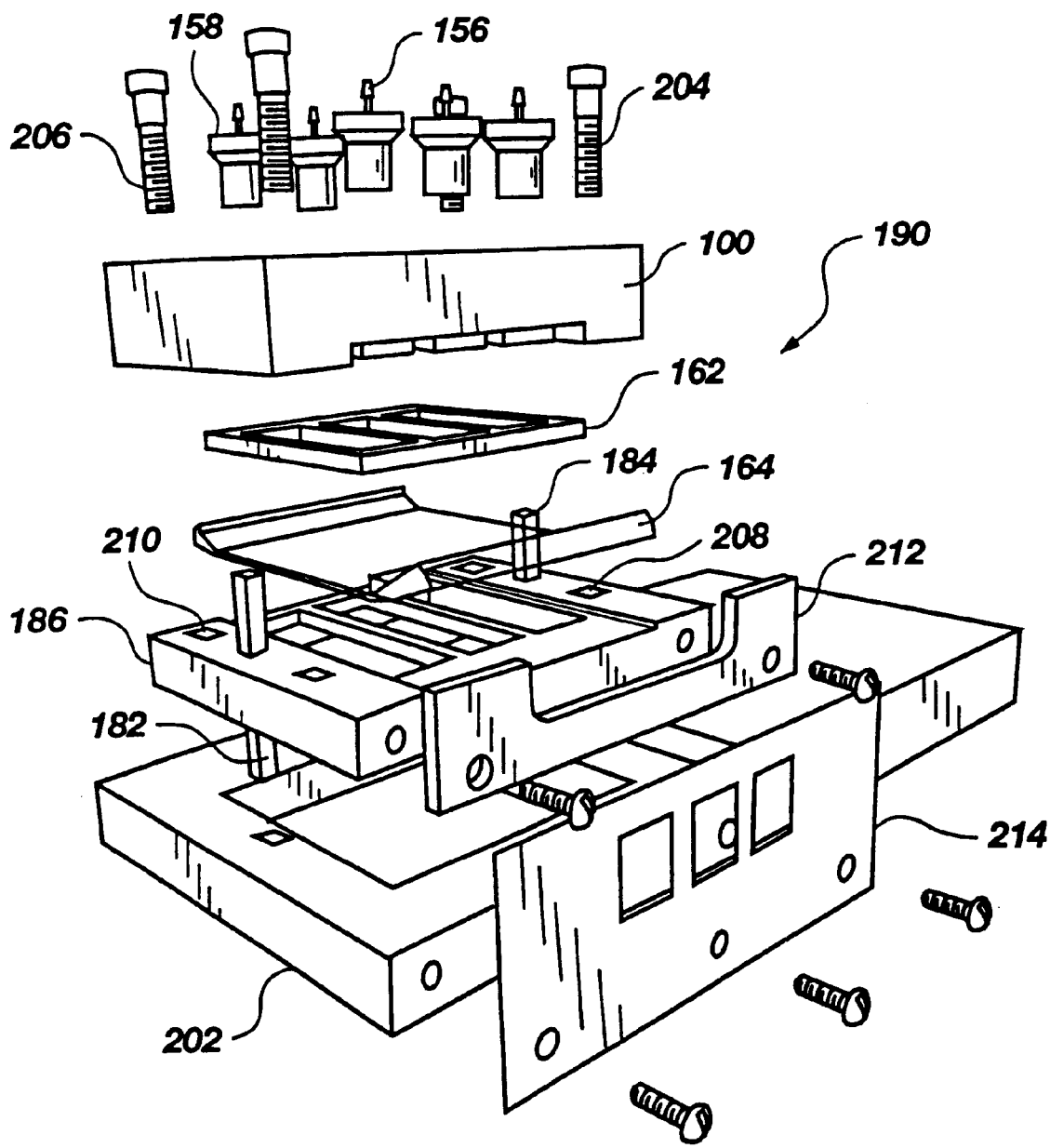
FIG. 4 depicts an enlarged, exploded, perspective view of a biosensor according to the invention.

In the depicted embodiment, the apertures 108–118 associated with the respective reservoirs 102–106 fluidically communicate the recessed portions 120–130 of the reservoirs with a pair of respective receptacles 144, 146, 148, 150, 152, 154 (shown by construction lines in FIG. 1) for receiving fluid inlet/outlet ports 156, 158 which are associated with the flow cell top 100 (FIG. 4). Although the fluid inlet/outlet ports 156, 158 will be described with regard only to one reservoir, it is to be understood that the description applies likewise for the other reservoirs of the flow cell (if any).

As depicted in FIG. 4, the fluid inlet/outlet ports 156, 158 may be male threaded nipples which interact with corresponding threaded members (threads not shown) bored into the flow cell top 100. The open ends of the nipples are in fluid communication (e.g., by tubing or other conduit—FIG. 8) with a, for example, syringe pump (not shown). Other fluid tight arrangements between the ports and the flow cell top can be used, so long as the sample fluid communicates to the apertures 108–118. The liquid to be analyzed (e.g., whole blood, plasma, diluents, or mixtures thereof) can thus be injected and withdrawn from the reservoirs 102–106 by use of an, for example, oscillating pump (not shown).

As further depicted in FIGS. 1 and 4, the outer peripheries of the walls 132–136 also partially define a recess 160 formed in the flow cell top. This recess 160 is formed to accept a gasket 162 (FIGS. 4, 5 & 11) which is more thoroughly described hereinafter. This gasket 162 cushions placement of a waveguide onto the flow cell top 100 and impedes slippage of the waveguide when associated with the flow cell top. As is also more thoroughly described herein, the gasket, preferably, does not serve as any part of the walls 132–136 to contain the liquid within a reservoir 102–106. The flow cell may be used with a quartz waveguide or, more preferably, with the hereinafter described plastic molded waveguide 164.

B. The Waveguide

Figure 6:
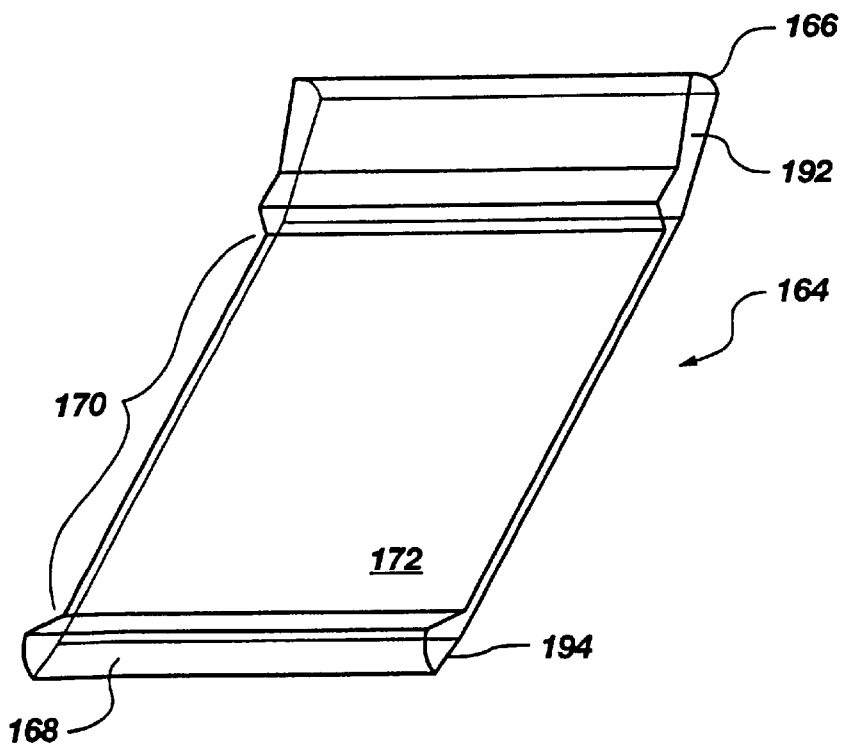
FIG. 6 depicts an enlarged view of a plastic, molded flat waveguide with integrated input and output coupling lenses.
Figure 7:
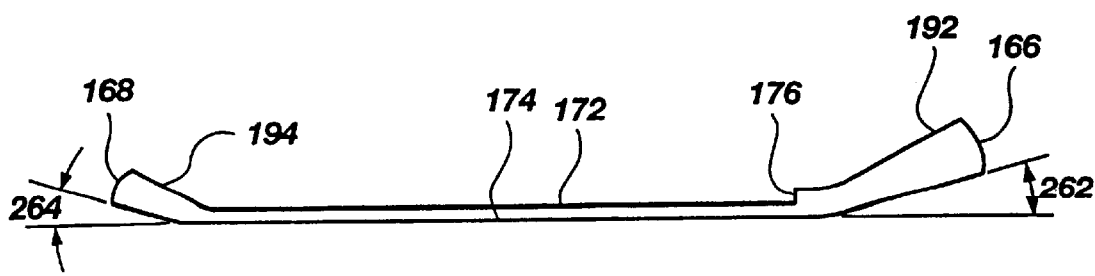
FIG. 7 is an enlarged side view of the waveguide of the preceding figure.
Figure 9:
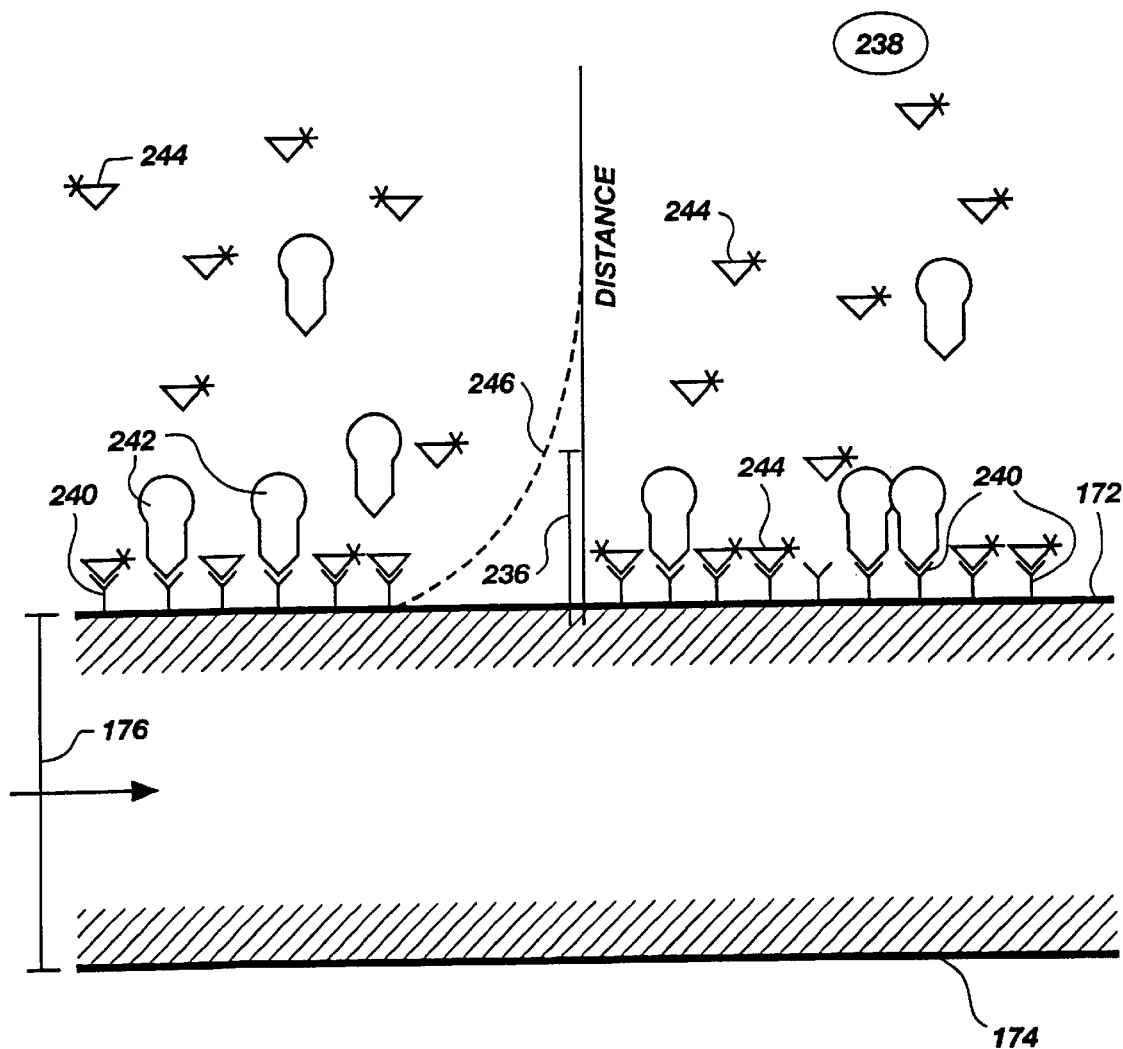
FIG. 9 is a stylized, enlarged side view of a portion of a waveguide and biochemical components of a competition immunofluorescent assay according to the invention.

As depicted in FIGS. 4, 6 & 7, a preferred waveguide 164 is a plastic molded waveguide (e.g., molded of an optical plastic) having integrated input 166 and output 168 coupling lenses. Such a waveguide 164 is preferably sled-shaped, having a planar (optical substrate) portion 170 with first 172 and second 174 parallel plane surfaces and an edge having a thickness 176 extending therebetween (FIG. 9). At least one of the waveguide surfaces 172 has a plurality of capture molecules 240 associated therewith (e.g., immobilized thereon as depicted in FIG. 9, although other methods of bringing the capture molecules into sufficiently close association with the surface may be used (e.g., by placing a strip immunoassay onto the waveguide surface, or using a fibrous "mat" with capture molecules attached to the fibers)). These surfaces 172, 174 should have the best optical smoothness possible. For example, surface waviness and roughness spacing should lie outside a range of about 65 nm to 195 micrometers ("$\mu$m"), while spacings close to 650 nm should be avoided (when 632.8 nm laser light is used). Surface roughness amplitude or "Ra" (theoretical surface plane to average peak or valley) should be less than 0.0065 $\mu$m (0.26 $\mu$in); however twice this amount is still functional. The thickness will typically be between 0.20 and one millimeter ("mm"), more preferably about 0.5 mm.

The edge of the planar portion has a receiving region (e.g., lens 166) for receiving light to be internally propagated. In the embodiment depicted in FIGS. 6 & 7, an input or receiving lens 166 is integrally adapted to the waveguide adjacent the receiving region at the "front" of the waveguide. Other methods of optically associating the lens to the planar portion could also be used. Surface specifications for such a lens or lenses are similar to the planar or "plate" portion of the waveguide. A maximum roughness amplitude of 0.013 to 0.025 $\mu$m (0.5 to 1 $\mu$in) is preferred. Preferably, machine lines should be parallel (vertical when looking at lens) to the long axis of the waveguide. Surface specifications for the side of the part and lens ramp areas are less stringent than the top and bottom surfaces of the plate structure.

In another embodiment (not shown), the lens (or lenses) is not integrally associated with the waveguide, but is adapted to interact optically with the waveguide, or multiple waveguides.

Alternatively, rather than using a lens to couple light into the waveguide, a grating could be used. Various gratings as well as methods for incorporating them into a waveguide are known. See, e.g., U.S. Pat. No. 5,480,687 (Jan. 2, 1996) to Heming et al. at column 4, lines 1–10, and column 6, line 20 to column 7, line 55, U.S. Pat. No. 5,081,012 (Jan. 14, 1992) to Flanagan et al., U.S. Pat. No. 5,455,178 (Oct. 3, 1995) to Fattinger, U.S. Pat. No. 5,442,169 (Aug. 15, 1995) to Kunz, and U.S. Pat. No. 5,082,629 (Jan. 21, 1992) to Burgess, Jr. et al. Gratings may be fabricated by a number of means including but not limited to: embossing, molding, photolithography, direct etch electron beam lithography, interference lithography, and phase shift lithography. Embossed gratings are mechanically stamped or thermally imbued onto a surface and thereupon affixed to a substrate. Photolithographic gratings are formed from the chemical development and etching of photoresist and substrate after masked illumination by an appropriate source. Interference and phase shift lithography are similar techniques which allow finer resolution of etched structures than does conventional photolithography. Ion or particle beam methods fabricate precise gratings by directly etching or "writing" a grating substrate with a stream of ions or molecular particles.

The grating itself can consist of an etched pattern of regular features in a metal film coated onto the planar portion of the waveguide or the front ramp. Standard diffraction gratings such as those used in spectrometers like "replica" gratings (gratings comprised of a dried epoxy coated with metal) can be used. The use of such grating couplers helps to avoid fabrication complexities associated with the use of a receiving lens or plasma-etched gratings. The procedure for applying such couplers is presently used to emboss holograms onto plastic credit cards, and, using such a process, the coupler could be mass produced at a relatively low cost.

Figure 19:
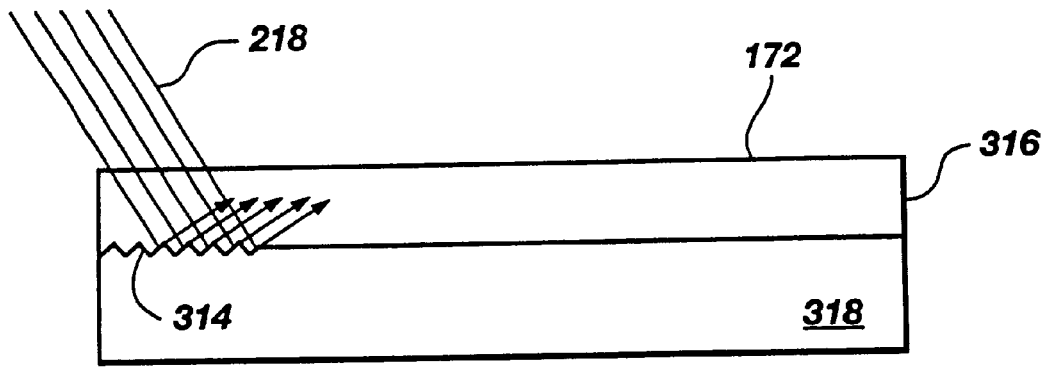
FIG. 19 depicts an enlarged, stylized, side view of a portion of a plastic film waveguide having an optical diffraction grating coupler.
Figure 20:
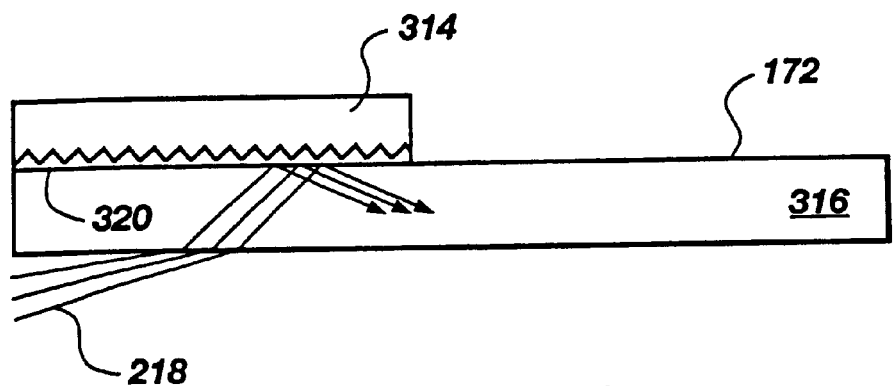
FIG. 20 depicts an enlarged, stylized, side view of a portion of a plastic film waveguide to which a separate optical diffraction grating has been associated.

In an alternative embodiment shown in FIG. 19, a corrugated waveguide with gratings 314 (>5 nanometers ("nm") deep or thick) is associated with (e.g., molded on, adhered to, or hot stamped onto or embossed onto) the receiving region of a plastic thin film waveguide 316 (or a cast thin plastic planar waveguide) associated with (e.g., adhered to) a lower index substrate 318. Although in the depicted embodiment, the grating 314 is positioned between the thin film and the lower index substrate, other orientations such as applying the grating to the surface 172 of the thin film waveguide could also be used. Also, alternatively, the light could be directed into the waveguide from a different direction. In any event, the grating receives light 218 to be internally propagated. In such a case, the waveguide portion will typically be made of a transparent optical plastic and have a thickness of from about 10 micrometers to about 200 micrometers, preferably about 125 micrometers. In the case of extremely thin waveguide films (e.g., about 10 to 25 $\mu$m), the resulting film may be attached to a preferably rigid, open support structure 317 (FIG. 20). Alternately, the resulting thin film may be affixed to a supporting substrate having a lower index of refraction than the film (FIG. 19).

From efficiency measurements, it can be determined that for an integrated optic waveguide-fluoroimmunoassay, the most efficient etch depths are about 1.5 times that of the grating period. For diffraction to occur in a grating, the period d should be on the order of the wavelength of light (lambda). Given the pathlength difference, $\delta$, between the light rays from two neighboring grating features (slits, rigids, and the like), a constructive interference pattern is established by the light leaving the grating when $\delta$ is an integer multiple, m, of the wavelength.

$$\delta = d(n_t \sin \Theta_t - n_i \sin \Theta_i) = \text{lambda}(m)$$

wherein d is the grating period, $\Theta_t$ and $\Theta_i$ are the transmitted and incident angles at the grating interface (measured relative to the surface normal), and $n_t$ and $n_i$ are the refractive indices of the transmitting and incident mediums (i.e., the waveguide and the substrate). Using this formula, one determines that the incident angle for coupling 632.8 mn light is 38.03° when the grating period is 0.7 $\mu$m.

The angle of incidence of light from air into the lowest order made of the waveguide and the groove density into waveguide films can be calculated by the use of the equation above, and was determined to be 4.6°, 27.4° and 57.2° for polystyrenes having densities of 2400 g/mm, 1800 g/mm, and 1200 g/mm, respectively, for incident light of 632.8 $\mu$m wavelength.

In still other embodiments, laser light may be prism-coupled onto an integrated optic waveguide ("IOW") (not shown), end-fire coupled (i.e., direct focusing of light into the waveguide), or taper-coupled (e.g., by use of an adlayer film tapered in thickness or refractive index, preferably in conjunction with a grating coupler) into the waveguide (also not shown).

In order to taper-couple light into the flow cell, a gentle tapered section (e.g., either curved or linear) can be used to "funnel" light into the end of a thin planar waveguide. A well-collimated input beam (e.g., a laser) couples into a multi-mode waveguide (e.g., about 50 µm in thickness) due to the "Law of Brightness" constraint (i.e. the product of the beam extent and numerical aperture is a constant through the taper). The taper may be also coupled with a lens.

The waveguide depicted in FIGS. 6 & 7 has a shelf or ridge 176. The ridge 176 abuts against an edge of the flow cell top when the waveguide 164 is functionally associated with the flow cell (FIG. 4). As shown (FIG. 1), the flow cell top 100 has two apertures 178, 180 which interact with registration members ("registration pins") 182, 184 of a second frame member ("flow cell bottom") 186 structured to interact with the flow cell top 100 and waveguide 164 in order to hold ("sandwich") the waveguide in place (FIG. 4).

Figure 8:
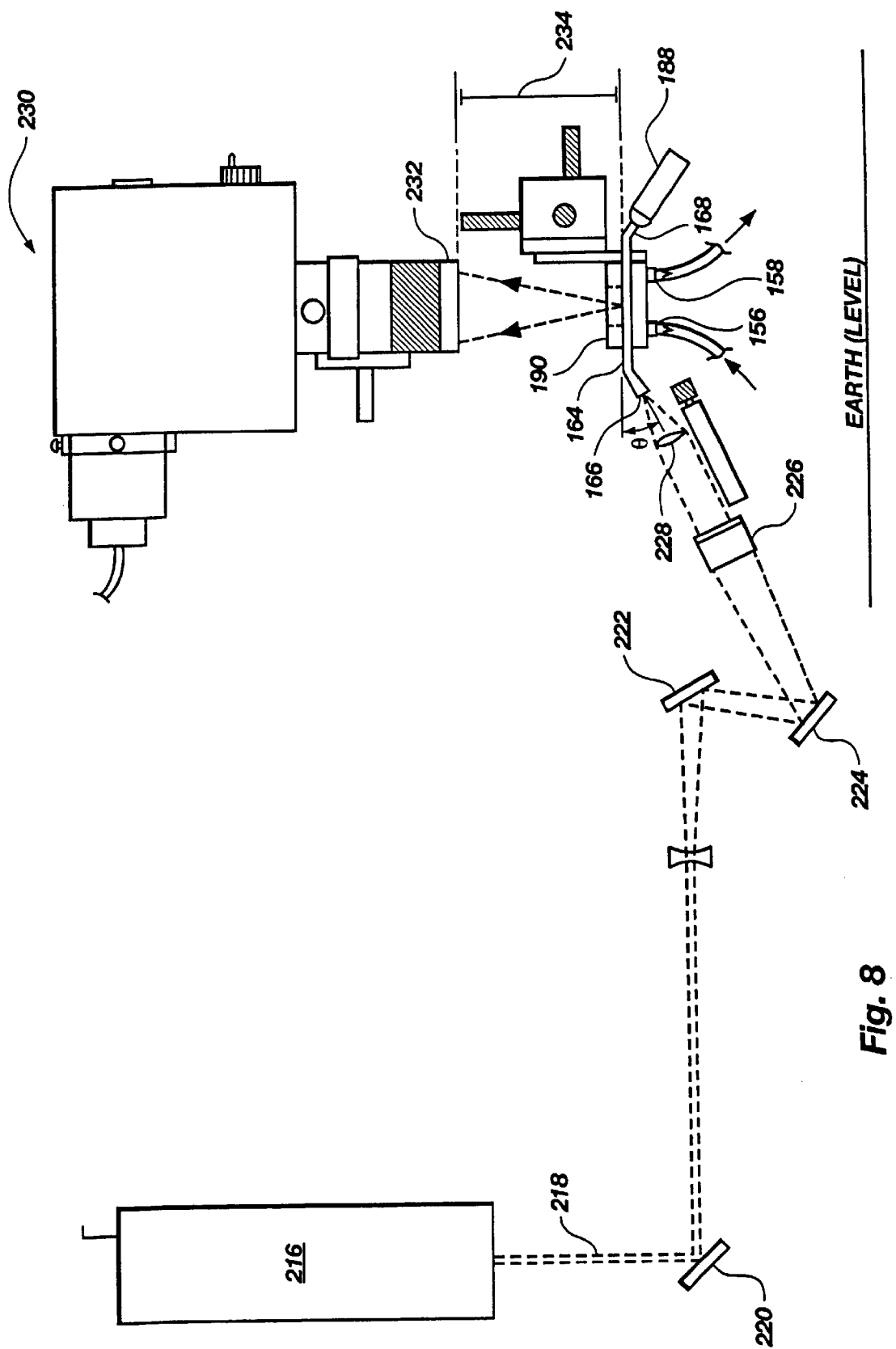
FIG. 8 is a schematic diagram of a fluorescent assay apparatus useful for practicing the invention, showing the flow cell assembly of FIG. 4 in a particularly useful orientation with respect to the earth.

Laser light preferably enters the receiving lens 166 at mean angle Θ (FIG. 8). The mean angle Θ will typically vary dependent upon the type of material used to form the waveguide and the optical properties of the media opposite both faces of the waveguide. When the waveguide or waveguide layer is made of polystyrene (e.g., NOVOCOR), then the mean angle will generally be less than 32°, e.g., 15° to 25°. Typical beam widths vary from 0.5 to 2.0 mm.

On the other side of the waveguide, an outcoupling 188 interacts with the rear or output lens 168 to ensure that light is detected (FIG. 8). The outcoupling 188 may be a single photodetector, multiple photodetectors, standard CCD (charge-coupled device) or like device. The light passing through the waveguide 164 and received by the outcoupling 188 is analyzed for quality and/or intensity. Unlike the end collection of light described in U.S. Pat. No. 4,582,809 to Block et al. (Apr. 15, 1986), in the present invention, the light may be detected at the end of the waveguide for two reasons. The first reason is as a quality control measure. The light passing through the waveguide may be measured so that the operator of the device knows that the biosensor has been properly placed in the apparatus and that the light source is still working. Alternatively, the device may be configured so that a predetermined strength of light must first be detected at the rear lens 168 before the apparatus will operate, again to ensure that the flow cell assembly ("biosensor"), generally 190, has been properly placed. The second reason for end detection involves calibration of the device to ensure that the amount of light traveling through the waveguide is uniform and, if it is not uniform to accommodate any differences. The light outcoupled from the lens 168 associated with the rear of the waveguide is preferably measured over the width of the lens to ensure that sufficient light is passing through the lens to create detectable fluorescence.

Preferably, a plastic waveguide such as that depicted in FIGS. 6 & 7 will be made (e.g., injection-molded) of an optical plastic such as polystyrene, polymethylmethacrylate ("PMMA"), polycarbonate or equivalent material, and will have a refractive index greater than 1.33 (the index of water being 1.33). The size of the waveguide will depend on its desired use.

Although the front lens ramp 192 and rear lens ramp 194 are shown in a "concave" or arced position relative to one another and the planar portion 170 (FIG. 7), the ramps need not angle towards a common center, and one of the lens ramps could be angled in the opposite direction from the plane of the planar portion, and the ramps would fall in roughly parallel planes (not shown).

In another embodiment (not shown), the waveguide includes a laminate of layers, one layer serving as a structural substrate, and the other (e.g., thin film SiON) serving to transmit the light, such as those disclosed in International Application No. PCT/US96/02662 (International Publication No. WO 96/26432, published Aug. 29, 1996) to the University of Utah Research Foundation. In such an embodiment, the structural substrate can be made of a plastic such as polystyrene, PMMA, polyvinyl chloride ("PVC"), polyimide, polyester, polyurethane, organically modified ceramics, polymers of diethylene glycol bisallyl carbonate, allyldiglycolcarbonate, polycarbonate, or equivalent material. The waveguide layer is preferably an optical plastic such as polystyrene, although it can be made of other suitable materials such as $TiO_2$, a mixture of $TiO_2$—$SiO_2$, $SiO_2$, ZnO, $Nb_2O_5$, $Si_3N_4$, $Ta_2O_5$, $HfO_2$, or $ZrO_2$. Waveguide layers such as $TiO_2$, $SiO_2$, or $Si_3N_4$ can be deposited by plasma chemical vapor deposition ("PVCD"), plasma impulse chemical vapor deposition ("PICVD") process, or the like.

C. Gasket

Figure 5:
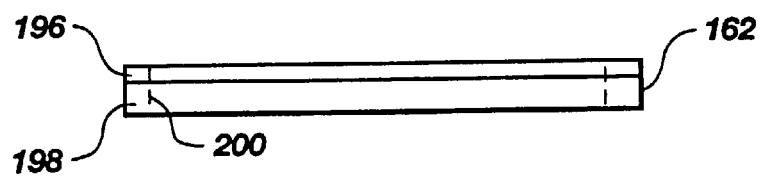
FIG. 5 depicts an enlarged, side view of a laminated gasket which interacts with the flow cell top of FIG. 1.

A gasket 162 is preferably seated between waveguide 164 and flow cell top 100 (FIGS. 4, 5 & 11). A preferred gasket 162 for use with the waveguide 164 with integrated lenses includes a clear TEFLON™ layer 196 adhered (e.g., with the use of a suitable glue or double-sided tape, e.g., MACTAC No. SB 1154 available from Morgan Adhesives Co. of Stow, Ohio, USA) to a silicon rubber gasket 198 shaped to fit the recess of the flow cell top. Alternatively, synthetic resin polymers (i.e. TEFLON-like materials) may be used. The depicted gasket 162 is configured with three internal openings (FIG. 11 and construction lines 200 of FIG. 5) which surround, but do not interact with, the reservoirs 102–106.

Upon assembly of the biosensor, in the reservoirs 102–106, the first planar surface 172 of the waveguide 164 constitutes a floor or ceiling (FIG. 8) of the particular reservoir, while the flow cell top 100 is formed to constitute the ceiling or floor and the walls. The orientation depicted in FIG. 8, wherein the planar surface 172 serves as a ceiling and lays level with the earth has been found to be especially useful, enhancing the ability of the device to detect the presence of target molecules in even whole blood over a shorter period of time (e.g., five to ten minutes), especially with oscillation. However, it is, of course, understood that the flow cell assembly 190 may be oriented in any position (e.g., vertical or any angle). Angling the flow cell assembly 190 assists in removing bubbles or heavy materials away from the waveguide 164, if desired. Alternatively, a dye can be incorporated into the sample solution for absorbing interfering signals. Although the reservoirs 102–106 are here shown to be generally rectangular in shape, other shapes could be used.

The gasket 162 is preferably made of a semi-rigid material having an index of refraction less than that of the waveguide material in the wavelength range of the exciting light. For best results, it is believed that the index of refraction of the gasket material should be as low as possible compared to that of the waveguide. For a waveguide made of quartz or glass, the index of refraction would typically be from about 1.46 to 1.52, higher for high-lead glass. A transparent (non-pigmented) silicon rubber (siloxane polymer) with an index of refraction of 1.35–1.43 is a presently preferred material for gasket 162. TEFLON™ or TEFLON-type materials such as PTFE (polytetrafluoroethylene) or FEP (fluorinated ethylene propylene) have indices of refraction of around 1.34–1.35, and may also be suitable for use as layer 196.

The other portion 198 of the gasket may be formed of an opaque (e.g., red or black) neoprene or silicon rubber material which is preferably biologically inert although due to the metal walls, it need not be.

D. The Flow Cell Assembly

Figure 10:
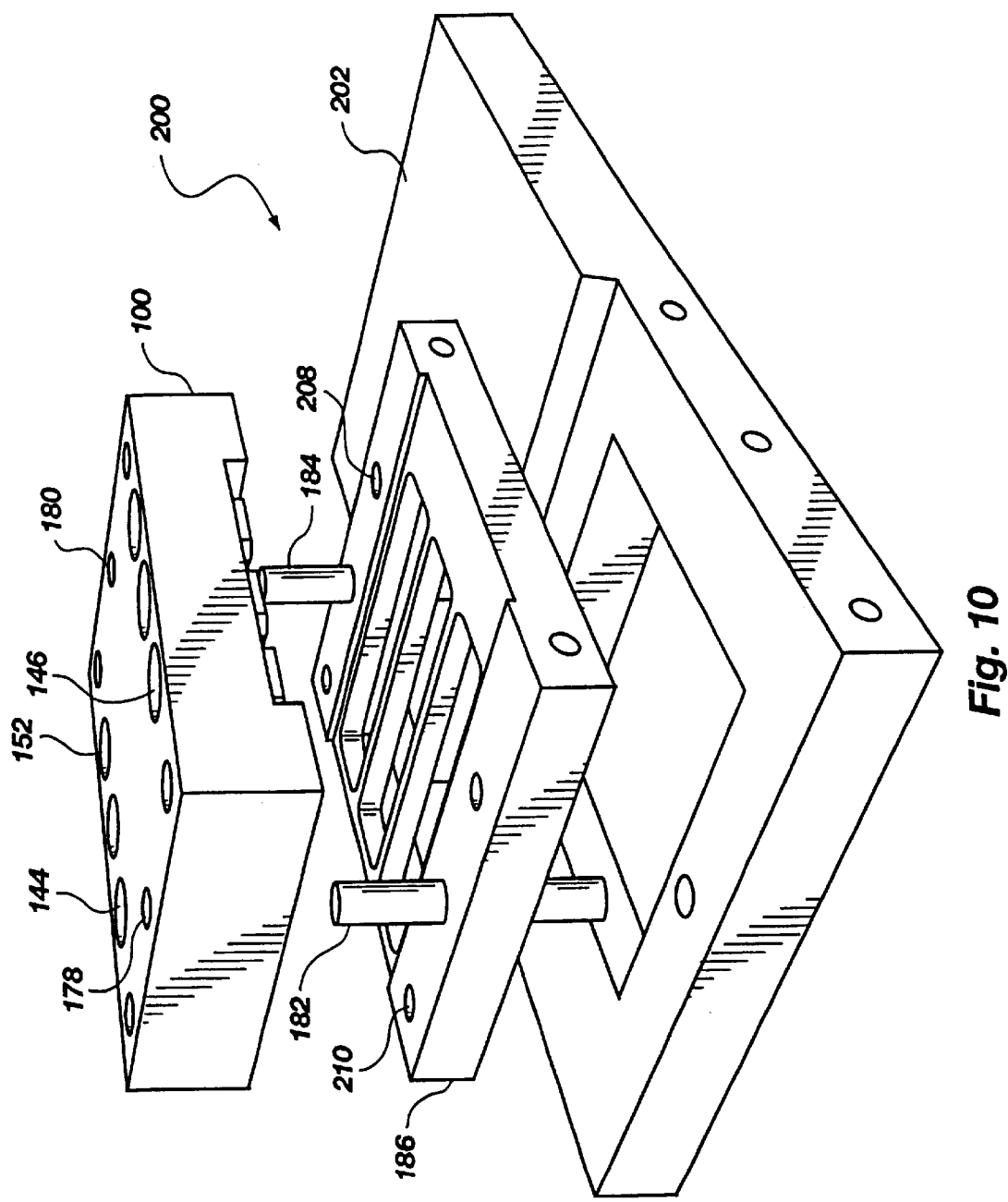
FIG. 10 depicts an enlarged, exploded, perspective view of the flow cell portion of a biosensor according to the invention.
Figure 18:
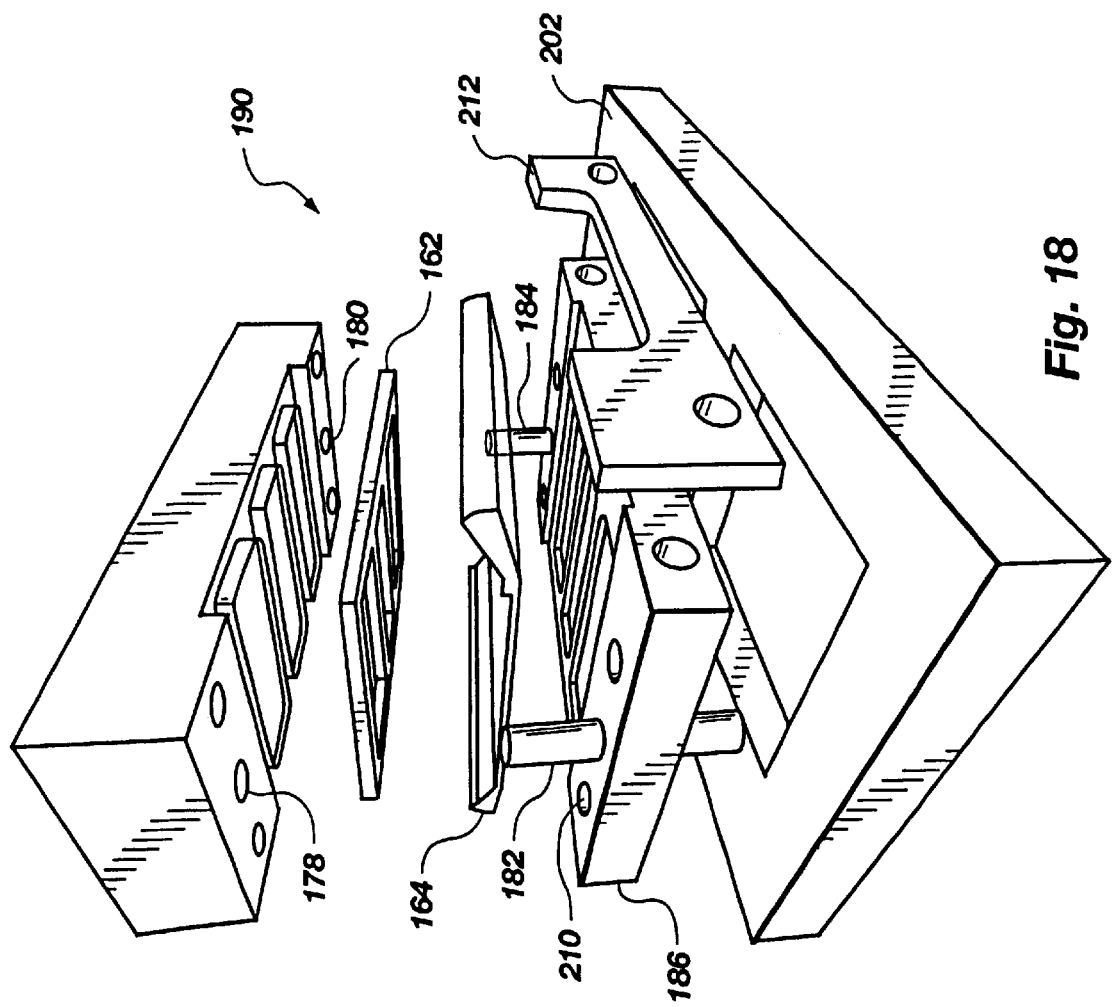
FIG. 18 depicts an enlarged, exploded, perspective view of a biosensor according to the invention.

As depicted in FIG. 18, a preferred flow cell assembly 190 according to the invention generally includes a flow cell portion (generally 200, FIG. 10), gasket 162, and waveguide 164. As shown in FIG. 10, the flow cell portion includes the flow cell top 100, flow cell bottom 186, and a flow cell stage (or "flow cell platform") 202. As shown in FIG. 8, and as more thoroughly described herein, these three components of the biosensor 190 are integrated with one another in such a manner that excitation light enters the front lens 166 of the waveguide 164, travels through the front lens ramp 192 and planar portion 170, and passes out of the rear lens ramp 194 and rear lens 168 to the outcoupling 188.

The flow cell assembly can also include means for associating the flow cell top 100 with the flow cell bottom 186 thus sandwiching the gasket 162 and waveguide 162 therebetween. The depicted means for doing so are threaded clamping bolts 204, 206 which interact with correspondingly threaded holes 208, 210 in the flow cell bottom 186. Of course however, equivalent means such as screws, nuts and bolts, clamps, snap fits, and the like could alternatively be used.

A waveguide registration plate 212 is shown associated with the flow cell bottom 186 (FIG. 4). The waveguide is reproducibly positioned between the flow cell top and bottom when aligned with the registration plate. Also depicted is a 3-channel beam mask 214 having three apertures for receiving a light beam.

E. The Apparatus

Once the flow cell 200, gasket 162 and particular waveguide 164 have been associated with one another, the thus formed biosensor 190 may be used in an apparatus for performing immunoassays such as fluoroimmunoassays. As depicted in FIG. 8, such an apparatus includes a light source 216 which provides a light beam 218 which is directed by means of mirrors 220, 222, 224 to an optical biosensor 190. The light source 216 may be an argon laser or laser diode capable of emitting at center wavelengths of between 488 and 514.5 nm and 600 to about 900 nm (e.g., 633 nm), respectively.

The embodiment of FIG. 8 further includes a 45° angle mirror 226 which is positioned for assisting in focusing the beam 218 onto the input lens 166 of a particular biosensor 190 if desired. The biosensor 190 has an optical substrate with one end 166 positioned to receive light from beam 218. In the case of a non-integrated quartz waveguide, a focusing lens 228 is preferably positioned between angle mirror 226 and the biosensor 190 for focusing light from beam 218 onto the end of the biosensor. Focusing lens 228 is removable, and is depicted mounted on an X-Y translation unit so that its position may be adjusted for best focusing. Furthermore, the translation unit can be moved to adjust the angle Θ for waveguides of differing composition. A significant portion (in the case of the quartz waveguide, the entire portion) of the optical substrate 164 is of a generally planar shape having two planar surfaces spaced by a width 176 as shown in FIG. 9, which is more thoroughly described herein.

Light detection means, generally 230, are positioned to detect fluorescent light emitted from the biosensor 190. As more thoroughly described herein with regard to FIG. 9, the emitted light is reflective of the concentration of a selected analyte in a sample. The light detection means 230 depicted in FIG. 8 includes a collection lens 232 positioned to collect the emitted fluorescence from a direction substantially orthogonal to the direction of propagation of light 218 through optical substrate 164.

The distance 234 between collection lens 232 and optical substrate 164 is selected as known to those skilled to maximize the collection of light emitted from the region of evanescent light penetration while at the same time imaging this light onto the face of the photodetector. The light collected by collection lens 232 is then sent to detection means 230, which responds by outputting signals reflective of the level of collected fluorescent light.

Detection means 230 may be any type of photodetector useful to detect light in the wavelength region spanning the wavelength range of the emitted fluorescence, as known in the art. However, in a preferred embodiment for simultaneous multi-analyte assays, detection means 230 is an imaging-type detector providing direct imaging of each of the fluorescent signal(s) originating in the evanescent zone 236 (FIG. 9). In the apparatus of FIG. 8, detection means 230 is a CCD detector which produces a signal. Such imaging signal collection provides simultaneous measurement of multiple samples in a much simpler way than a system in which a separate optical element is needed to read each well or patch. The present imaging detection system also provides for collection of emitted fluorescence directly from the evanescent zone 236, rather than via evanescent penetration of the fluorescence into the waveguide (FIG. 9).

Alternatively, detection means 230 may be a photomultiplier, a semiconductor photodiode, or an array of such detectors. In embodiments other than a CCD, an array is generally preferable to a single detector for some purposes. With an array of small detectors, the user can determine that the maximum fluorescence is being detected and is not inadvertently missed due to misalignment of the collection and detection optics. Optionally, a grating spectrograph is coupled to the CCD or other detection means to provide spectral analysis of the detected light. In that case, means are also provided to integrate the signal function around each peak to determine the total collected fluorescence from a sample. Alternatively, in an embodiment for use in a setting such as in a testing laboratory, and for which all the parameters of the assay have been standardized, the spectrograph may be replaced by a filter which passes only wavelengths in the region of tracer fluorescence.

As is better seen in FIG. 9, optical substrate 164 is embodied as a planar portion of a waveguide having at least one planar surface 172 spaced from a second surface 174 by a width 176. At least one surface 174 is disposed in contact with a sample solution 238. Capture molecules 240 are immobilized on the exposed surface 172 of the waveguide. In one embodiment, the sample solution 238 contains a plurality of analyte molecules 242 of a selected analyte which also includes tracer molecules 244. The tracer molecules can be incorporated into the sample solution by, for example, admixing them with the sample solution before incorporation into the assay or by "drying" the molecules onto the waveguide surface without actually chemically binding them to the surface 172 (or at least not binding them permanently as would be the case when the tracer molecules are associated with the surface by use of a water soluble component (e.g. a soluble sugar that does not interfere with the particular interaction between capture and tracer molecules)). The capture molecules are chosen or constructed to bind to a binding moiety present on each of the analyte molecules 242. The tracer molecule 244 is a molecule chosen to be complementary (in a binding sense) with the capture molecules and is constructed to emit fluorescent light in response to stimulation by light of the appropriate wavelength (e.g., by tagging the capture molecule with a fluorescent label). The level of fluorescence emitted by the tracer molecules 244 is a measure of the amount of analyte bound to the capture molecule and is thereby reflective of the concentration of analyte molecules 242 in the solution.

When light is being propagated in the waveguide 164 and internally reflected at the surfaces 172, 174 an evanescent light field is produced having an intensity curve 230 which drops off with distance from the surface 172, as diagramed relative to a distance axis 232 and a horizontal axis 234 (not to scale). Evanescent light intensity varies along axis 232, co-linear with distance. An excitation zone 236 is the only region of the solution in which the evanescent light intensity is sufficient to excite a significant or detectable fraction of tracer molecules 244 (not to scale). Tracer molecules 244 outside zone 236 will contribute little or no induced fluorescence. Excitation zone 236 is typically between about 1000 and 2000 Å in depth.

Capture molecules 240 are reactive with the analyte molecules 242, and may be whole antibodies, antibody fragments such as Fab' fragments, peptides, epitopes, membrane receptors, whole antigenic molecules (haptens) or antigenic fragments, oligopeptides, oligonucleotides, mimitopes, nucleic acids and/or mixtures thereof. Capture molecules 240 may also be a receptor molecule of the kind usually found on a cell or organelle membrane and which has specificity for a desired analyte, or a portion thereof carrying the analyte-specific-binding property of the receptor.

The capture molecules 240 may be immobilized on the surface 172 by any method known in the art. However, in the preferred embodiment, the capture molecules are immobilized in a site-specific manner. As used in this application, the term "site-specific" means that specific sites on the capture molecules are involved in the coupling to the waveguide, rather than random sites as with typical prior art methods. Int'l Publ. No. 94/27137, which has been previously referenced, details methods for site-specific immobilization of capture molecules to the surface of the optical substrate by means of a protein-resistant coating on the substrate.

The waveguide can be designed so that multiple (e.g., four) different assays can be performed on the same sample. This is accomplished by immobilizing different types of capture antibodies on different regions of the waveguide, a process referred to as patterning. Three different patterning methods appear suitable for immobilizing antibodies to the polystyrene sensors—gasketed multi-well coating tray, liquid jet printing and photolithography. In the former, a machine similar to an ink jet printer is used to spray reagents onto a specific region of the waveguide; in the latter, ultraviolet light is used to photochemically cross-link antibodies to selected regions.

One immobilization chemistry is based on physical adsorption of antibodies to the waveguide. In one method, an antibody is briefly exposed to acidic conditions just prior to immobilization. It has been shown that this acid pretreatment step improves the antigen-binding capacity (AgBC) of immobilized antibodies by up to 3-fold in some cases. This immobilization chemistry is relatively simple and compatible with gasketed multi-well coating tray or liquid jet printing technology, but in some cases it exhibits a higher degree of non-specific binding than other methods.

The other two immobilization chemistries are based on a family of tri-block polymers of the form PEO-PPO-PEO, where PEO stands for poly(ethylene oxide) and PPO stands for poly(propylene oxide). These surfactants are sold under the trade name PLURONICS and come in a variety of chain lengths for both the PEO and PPO blocks. The PPO block is significantly more hydrophobic than the PEO blocks and adsorbs readily to non-polar surfaces such as polystyrene, leaving the PEO blocks exposed to bulk solution. The free ends of the PEO chains exhibit high mobility, literally sweeping proteins away from the surface.

In both the second and third immobilization chemistries, the surface of the waveguide is coated with pluronics before attachment of antibodies, but the two chemistries differ in how the antibodies are attached. In the second chemistry a photochemical cross-linking agent is used to conjugate antigen-binding fragments (Fab') to the PEO blocks, making this method suitable for patterning by photolithography. In the third chemistry, Fab' fragments are attached to pluronics using a chemical cross-linking agent, making this method compatible with gasketed multi-well coating tray or liquid jet patterning. The photochemical cross-linking method was evaluated with two different PLURONICS (F108 & P105) and two different photochemical crosslinkers (BPM and BPIA). While acceptable levels of total antigen binding can be obtained with all four pairwise combinations, an unacceptable level of NSB may be obtained when antibodies are immobilized to F108 using the BPIA crosslinker. The other three pairwise combinations give very low levels of NSB (about 1.5% of total binding). Furthermore, the P105/BPM pair is especially good, giving an undetectable level of NSB.

In FIG. 9, a competition assay scheme is depicted (also termed a displacement assay). However, as will be apparent to the skilled person, alternate assay schemes such as sandwich assays may be performed with the present apparatus. See, e.g., U.S. Pat. Nos. 4,376,110 and 4,486,530 to Hybritech, Inc.

In the embodiment of FIG. 9, the competition immunoassay has tracer molecules 244 constructed such that the capture molecules 240 will bind tracer molecules 244 in place of analyte molecules 242. Higher concentrations of analyte molecules 242 will cause most of the tracer molecules 244 to be displaced into the surrounding solution from capture molecules 240, thus reducing the number of tracer molecules within excitation range 236 of the substrate 164. This reduced binding of tracer molecules in turn reduces the amount of fluorescence. In contrast, lower concentrations of analyte molecules 242 will allow tracer molecules 244 to bind to capture molecules 240, and thus to be held within the excitation range 236.

In tests conducted with the point-of-care cardiovascular marker CK-MB (associated with acute myocardial infarction) on both plasma and whole blood, the results were comparable (taking into consideration diffusion and viscosity differences).

In the embodiment of the apparatus of FIG. 8, measurements of fluorescence are made by spectroscopy. Fluorescence detection was done with a monochromator (SPEX Industries, Inc., Model 1680C) and a CCD (Photometrics Ltd. Series 200, or CH-250). Alternatively, light source 216 can be any light source emitting at the wavelength desired for excitation of selected fluorescent dyes. Also, once an assay procedure has been validated and standardized, it may not be necessary to measure the fluorescence spectrum or spatial distribution of fluorescence. The detection means may be simplified in accordance with the minimum requirements of the assay.

In another alternate embodiment, light source 216 is a laser diode emitting in the red wavelength region of 600–700 nm which is commercially available. The laser diode may provide about 12 milliwatts of power with a peak emission wavelength of about 635 nm. Laser diodes emitting at 633 nm are also available and can be used. For an embodiment using a wavelength in this region, it is necessary to use dyes such as cyanine dyes, whose fluorescence can be stimulated by excitation with wavelengths in the red spectral region. An example of such a dye is the fluorescent dye CY5, available from Biological Detection Systems, Inc., Pittsburgh Pa. (catalog no. A25000). The CY5 dye can be conjugated to the desired tracer molecule by the manufacturer's instructions and/or with a kit available from BDS. A second dye, CY7, may also be suitable. The dyes and methods for conjugating are also characterized in the paper by Southwick, P. L., et al., titled "Cyanine Dye Labelling Reagents—Carboxymethylindocyanine Succinimidyl Esters", *Cytometry* 11:418–430 (1990). The use of laser diodes as a light source permits the biosensor and waveguide to be formed of plastic, which considerably reduces the expense of manufacture and facilitates the integral molding of the semi-cylindrical lens with the waveguide and reservoirs.

Different labels can be used which emit light at different wavelengths if desired. In such a circumstance, different types of capture molecules (e.g., antibodies reactive with different antigens) can be immobilized to the surface so that the waveguide can be used to detect more than one molecule to be detected. In such a case, multiple wavelengths can be detected by multiplexing the signal from the waveguide.

Figure 24:
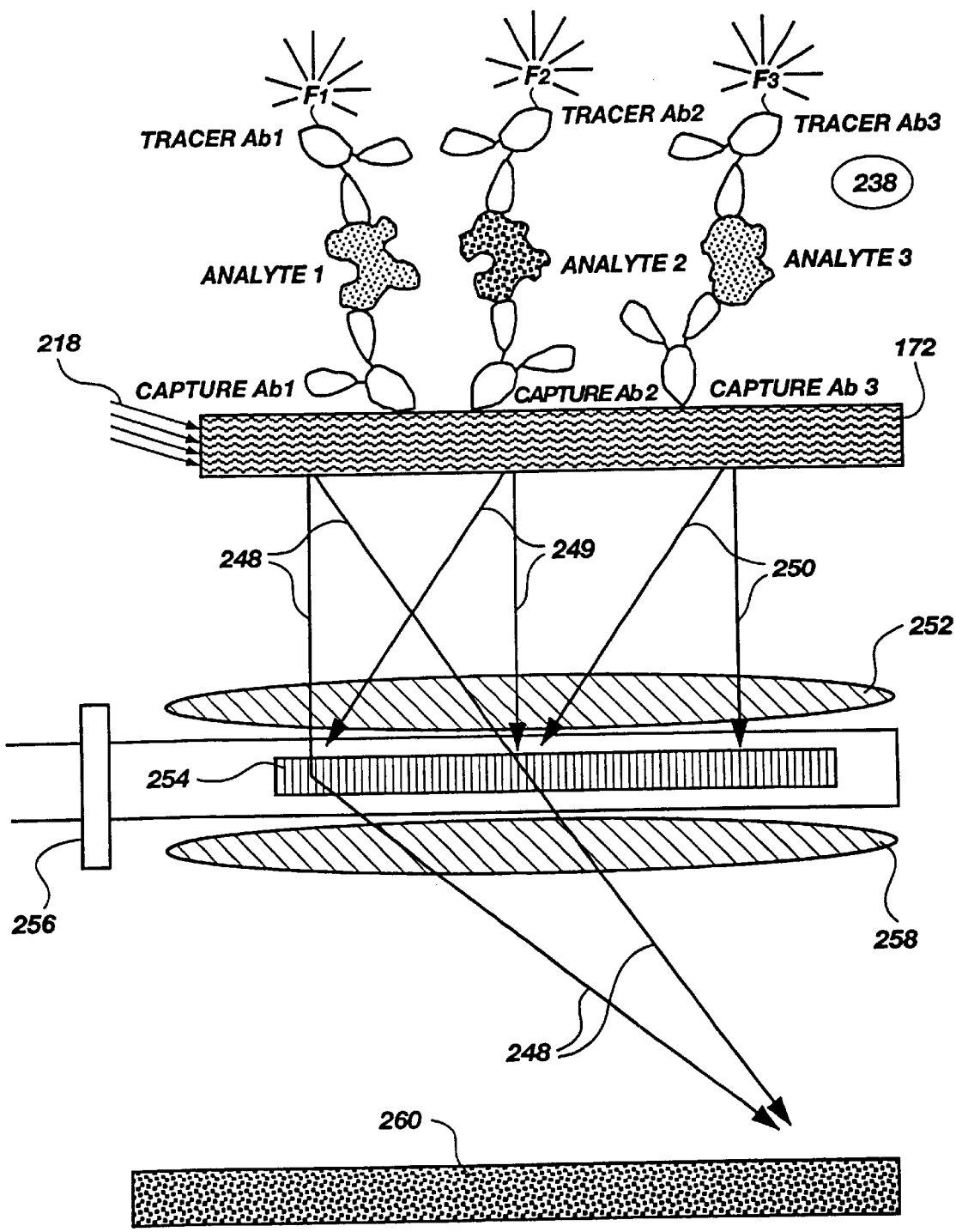
FIG. 24 is an enlarged, stylized illustration of wavelength- and spatially-resolved detection of fluorescence emitted from a planar waveguide sensor using different capture molecules and tracer molecules for detecting different analytes of interest in a sample solution.

FIG. 24 stylistically illustrates simultaneous wavelength- and spatially-resolved detection of fluorescence emitted from a waveguide sensor using different capture molecules (Capture $Ab_1$, Capture $Ab_2$, Capture $Ab_3$, ... Capture $Ab_x$), tracer molecules (Tracer $Ab_1$, Tracer $Ab_2$, Tracer $Ab_3$, ... Tracer $Ab_x$), and labels ($F_1$, $F_2$, $F_3$, ... $F_x$) with the purpose of detecting different analytes of interest ($Analyte_1$, $Analyte_2$, $Analyte_3$, ... $Analyte_x$) in a sample solution 238.

In the depicted embodiment, the device works as otherwise herein described, but each tracer molecule (e.g., Tracer $Ab_1$, Tracer $Ab_2$, Tracer $Ab_3$, ... Tracer $Ab_x$) is labeled with a different colored flourophore ($F_1$, $F_2$, $F_3$, ... $F_x$).

The waveguide is illuminated by one or more different wavelengths of light 218 appropriate to excite all the fluorophores located within the evanescent region of the waveguide. In one configuration, the emissions from the different fluorophores are distinguished using bandpass filters. Light rays 248, 249 and 250 are emitted from the respective labels on the tracer molecules. This light then passes through a lens 252 collimates the emitted light onto a band pass filter 254 selective for the wavelength emitted by the particular tracer molecule label, in the depicted case, Tracer $Ab_1$. A filter switching member, such as a wheel 256, houses, for example, three different band pass filters—each selective for a different fluorophore label. Thus, only the light rays 248 emitted by Tracer $Ab_1$, pass through the filter 254. If spatial resolution is desired in addition to wavelength selection, the light 248 passing through the filter 254 passes through a second lens 258 which images the light 248 onto a spatially-resolved photodetector 260 such as a CCD or diode array. If only wavelength resolution is desired, the photodetector 260 may be a single spatially-integrating device, and lens 258 may be optionally omitted Alternatively, the wavelength selectivity may be accomplished by one of several means instead of a filter wheel, such as employing a diffraction grating, a prism, or an acousto-optical modulator to angularly separate the different emitted wavelengths and thus direct them to separate individual photodetector elements whose outputs are representative of the signal strengths in each wavelength band. In another arrangement which avoids the use of the rotating filter wheel, stationary beam splitters are employed to direct portions of the emitted light through stationary filters placed in front of individual photodetector elements.

Alternatively, if the excitation wavelengths of the different fluorophores are sufficiently separated without appreciable overlap, the light source may sequence in time through each excitation wavelength. The emitted light at any given time is related to the signal strength of the fluorophore set whose excitation wavelength is chosen at that particular time, and no further wavelength selective devices, such as filters, are needed.

The invention is further explained by the following illustrative examples.

EXAMPLES

Example I

A waveguide with integrated lenses, such as that depicted in FIGS. 6 & 7, was injection molded in a clean environment from a transparent, general purpose polystyrene. The waveguide had a length of 38 mm, and a width of 25 mm. The thickness 176 of the planar surface 170 was a consistent 0.5 mm. The ridge or "shelf" had a height of 1.3 mm. The front lens and rear lens had bottom edges co-planar with their respective centers of curvature. The front lens horizontal angle 262 was about 15°. The rear lens horizontal angle 264 was about 19°. The radii of curvature of the front and rear lenses were about 3.2 mm and 1.6 mm respectively. The mean angle $\Theta$ of the front lens was 21°. The mean angle of the rear lens was about 24°.

Example II

A flow cell top, such as that depicted in FIGS. 1–3, and 8, was made of hard black anodized 6061-T6 aluminum. It contained three reservoirs each of which had a 0.25 mm (0.010 in.) thick wall surrounding it, a flat floor in middle, two half-capsule shaped recesses at either end 1.6 mm (1/16 in.) in width, and ports 1.6 mm (1/16 in.) in diameter running into the center of each recess. The ports opened into a #10-32 (standard thread, not NPT) connector which ran out to the opposite face of the flow cell and was 5.1 mm (0.200 in.) deep. A 90° countersink 266 (FIG. 2) was given at the surface of the port connector (a plastic barbed tubing connector screwed into the port connector and sealed on the countersink). On both sides of the array of reservoirs were two raised platforms which were referred to as lands 268, 270. Each land had three holes running through the thickness of the part. The four #31 clamping holes 272, 274, 276, 278 were formed (i.e., drilled through). The two apertures 178, 180 were drilled and reamed to achieve a close sliding fit with 2.4 mm (3/32 in.) nominal four-sided pins 182, 184 press fit into the second frame member 186.

Example III

A gasket 162, such as that depicted in FIGS. 4, 5, and 11, was made as a composite structure laminated from 1.6 mm (1/16 in.) silicone rubber sheeting and 0.076 mm (0.003 in.) self-adhesive FEP film (total thickness: 1.676 mm (0.066 in.) nominal). Its outer dimensions were about 25 mm (1 in.) by 25.40 mm (1.000 in.) and it had three internal openings which corresponded to the flow cell reservoirs. The gasket was produced using a waterjet cutter and was seated on the flow cell such that the FEP layer faced away from the flow cell surface.

Example IV

A second member 186, such as that depicted in FIGS. 4, 10, 12, 13 and 18 was made from hard black anodized 6061-T6 aluminum. It contained three internal openings 280, 282, 284 which corresponded to the three reservoirs 102, 104, 106 of the flow cell 100 (but were slightly longer). The internal openings were positioned in a shallow depression (0.46 mm (0.018 in.) deep) 286 which seated the waveguide, and allow evanescent light emitted from any reacting tracer molecules on the waveguide surface to be detected by the detection means 230. As with the flow cell 102, two lands 288, 290 resided on either side of the internal openings, each land having three holes. Four clamping holes (e.g., 208, 210) were drilled through and tapped to #4-40 to receive thumb screws. Two apertures were drilled through to receive a 3.2 mm (⅛ in.) nominal dowel which was press fit into the hole. The dowel was stainless steel and projected approximately 7 mm (0.280 in.) above the top surface and 6.6 mm (0.260 in.) below the bottom surface of the second member. The exposed dowel was machined down to 2.4 mm (3/32 in.) nominal diameter and was squared off to produce a low-friction locating pin 182, 184. The bottom aspect of the secondary member was milled out to provide a single large window 292 for emitted fluorescence from the waveguide. The front surface of the secondary member contains two mounting holes 294, 296 #2-56 drilled and tapped to a depth of about 4 mm (0.15 in.) to fasten the flow cell registration plate 212. The registration plate, depicted in FIG. 14, is a simple U-shaped bracket which was produced from 1.6 mm (1/16 =1 in.) nominal 6061-T6 aluminum plate. It contained two #42 holes which corresponded to the holes on the front of the second member. The purpose of the registration plate was to provide a lateral hard-stop for the waveguide during clamping into the flow cell. The upright arms of the part contact the waveguide at the outer edges of the input coupling lens while allowing unimpeded coupling with the incoming laser beam.

Example V

A stage 202, best depicted in FIGS. 15–17, is a plate-like structure which was made from hard black anodized 6061-T6 aluminum. The receiving site 298 of the part was down-stepped and contains a single rectangular internal opening. Three #2-56 drilled and tapped holes 300, 302, 304 were positioned on the front of the part which were used to fasten a laser beam mask (not shown). Two #10-32 holes 306, 308 were drilled to a depth of 19 mm (0.750 in.) on the right side of the part to mount the stage to the test apparatus. The internal opening had beveled front 310 and rear 312 sides. Located on either side of the window were two 2.4 mm (3/32 in.) apertures (analogous to those in the flow cell) which allowed the clamped flow cell and second member to be mounted to the stage 202.

Example VI

The waveguide and integrated lenses of EXAMPLE I, the flow cell top of EXAMPLE II, the gasket of EXAMPLE III, the second member and registration plate of EXAMPLE IV, and the stage of EXAMPLE V were associated as in FIG. 4. A hard, black anodized coating was added to the parts with a nominal build-up of 0.0025 mm (0.001 in.), however, the assembly 190 was checked as much as possible prior to anodization to maximize the probability of proper fit.

The gasket was cut to correspond to the outside dimensions of the three reservoirs 102–106 of the flow cell top 100. The silicone rubber surface contacted the flow cell and the FEP surface contacted the waveguide when the assembly was clamped. Any flash present on the gasket which interfered with seating or which came over the top of the walls was carefully trimmed back with a razor knife (the top of the dam was exposed to the surface of the waveguide, but did not touch it; flash from the gasket can interfere with proper clamping).

The waveguide 164 was seated in the shallow depression in the second member 186. The waveguide fit into the depression with minimal lateral movement, but without compression or pinching. A small amount (e.g., less than about 0.1 mm (0.003 in.)) of lateral movement was acceptable. If pinching occurred, additional milling to the walls of the depression was necessary to allow proper seating.

To insure that the waveguide 164 was reproducibly positioned directly beneath the flow cell, it was butted up against the registration plate 214 after being seated in the secondary member 186. Contact with the registration plate 214 was only at the outermost corners of the front lens; no contact with the injection mold stub on the underside of the front lens occurred (injection mold may be designed to place resultant stub at an alternate location). The front of the second member may need to be milled to ensure the waveguide sits directly beneath the flow cell when in contact with the registration plate.

After seating the gasket into the flow cell and positioning the waveguide on the second member, the flow cell was mated with the second member by engaging the locating pins into the apertures in the flow cell. When fully engaged, but without adding additional clamping force (i.e., the gasket was not compressed), there was a 0.15 mm (0.006 in.) gap between the lands of the flow cell and the lands of the second member. When fully clamped with four thumb screws such that the lands are in contact, the gasket is compressed 0.15 mm (0.006 in.). The flow cell and second member readily separated using manual force; no sticking occurred, but a thin coat of lubricant may be used on the pins if necessary. It may be desirable to slightly countersink the press fit hole on the second member and/or the aperture on the flow cell to avoid burrs or bulges which might impair mating of the two parts.

The locating pins from the bottom of the second member readily aligned and fit into the apertures on the stage. No perceptible play existed between the parts when mated. As with the flow cell and second member fit, the second member and stage readily separated using moderate manual force.

Example VII

As shown in FIG. 20, onto a polystyrene sheet waveguide 316 (Scenic Materials, 125 μm thick, n=1.60) was adhered a piece of holographic diffraction grating 314 (Edmund Scientific #43226, 2400 g /mm, Al/N$_9$F$_2$ coated) with an index-matching cement 320 consisting of 10% polystyrene chips dissolved in toluene. Incoupling into the resulting waveguide was achieved with a helium-neon laser at an approximately 5° angle. The resulting coupling structure was thinner than a molded lens input coupler.

Example VIII

A. Waveguide Fabrication

Thin film channel waveguide layers of SiON were formed on grating etched quartz wafers in a manner such as that described in Walker et al. "Corning 7059, silicon oxynitride, and silicon dioxide thin-film integrated optical waveguides: In search of low-low, non-fluorescent reusable glass waveguides", *Appl.Spectrosc.*, 46: 1437–1441 (1992). Briefly, the wafers were introduced into a plasma impulse chemical vapor deposition ("PECVD") chamber (Texas Instruments) operating at 300° C., 50 W, and 1.25 Torr. The gases used were $SiH_4$, silane, nitrogen, ammonia, and nitrous oxide. SiON films were produced at a deposition rate of approximately 590 Å/minute for 25.42 min., yielding a film thickness of 1.5μ. As described in Plowman et al., "Femtomolar sensitivity using a channel-etched thin film waveguide fluoroimmunosensor", *Biosensors & Bioelectronics,* 11:149–160 (1996), nine parallel 1 mm ×65 mm channels are formed when etched into the SiON from an additional layer of photoresist. The resulting waveguide wafers were diced (Disco DAD-2H/6) into three rectangular pieces measuring about 2.5 cm×7.8 cm each with three waveguiding channels (although in this EXAMPLE, grating waveguides without channels were employed).

B. Grating Fabrication

Quartz wafer substrates (Hoya, Woodcliff Lake, N.J., QZ 4W55-325-UP) measuring 100 mm in flat length and 0.5 mm in thickness were cleaned at room temp. in a 6% solution of $H_2O_2$ in $H_2SO_4$. The wafers then received a HMDS vacuum vapor prime, were spin-coated with photoresist (Shipley SNR 200, Mass., USA) at a rate of 4200 rpm for 1 min. to produce a film approximately 0.7 mm thick and then soft-baked at 100° C. for 1 min. The negative resist was exposed to define 0.7μ periodic groove patterns using ultraviolet light (248 nm KrF excimer laser, Laser Stepper GCA-ALS, Tukesbury, Mass., USA) with a chrome-quartz mask (DuPont, Kokomo, Ind., USA) at a dose of 20 $mJ/cm^2$. The wafers received a post-exposure bake at 130° C. for 90 sec. Photoresist was developed in a solution of Shipley MF 312 (Mass., USA) at a normalization of 0.17, then spun dry. A 60 sec. 100° C. post-development bake was then performed. The resulting photoresist pattern was reactive ion-etched (8110 Reactive Ion Etcher, AME, Santa Clara, Calif., USA) with $O_2$ and $CHF_3$ gases at an etch rate of 450 Å/min. Etch times of 13.33, 17.77 and 22.22 min. were employed to produce grating etch depths of 0.6, 0.8, and 1.0μ giving aspect ratios of 0.8, 1.0, and 1.4, respectively. Residual photoresist was removed by $O_2$ plasma.

C. Testing

When used as light couplers for thin film IOWs, the gratings were roughly half as efficient as prisms in coupling laser light (the light source being a 2 mW He—Ne laser (632.8 nm, 10 mW maximum, Melles-Groit, Uniphase, Manteca, Calif., USA). Both approaches (i.e. prism and grating) detected samples with femtomolar concentration above background.

Example IX

An evanescent wave assay apparatus of the instant invention was compared with a standard ABBOTT STAT CK-MB IMx system.

A. Clinical Samples 63 clinical samples (submitted by physicians for hospital CK-MB testing) were obtained, and were assayed for CK-MB using the ABBOTT IMx system. The values thus obtained for each clinical sample was noted. Each sample was aliquoted into 0.550 ml sample size, assigned a lot number, and stored at −20° C.

B. Instrumentation/Assay Standardization

The samples were then assayed on a CK-MB system utilizing the biosensor 190 of the instant invention. CK-MB specificity was determined by spiking CK-MB stripped plasma (solid-phase absorption) with 1000 ng/ml CK-MM and CK-BB. Cross-reactivity with CK-MM was less than 0.1%. Standards were prepared by addition of a known mass quantity of recombinant CK-MB (Genzyme).

C. Monoclonal Antibodies

Monoclonal antibodies were as described by J. Ladenson, *Clinical Chemistry,* vol. 32, pp. 657–63 (1986). The capture antibody was coated onto the waveguide's surface with 2 hour incubation at room temp., at a concentration of 0.1 micromolar (diluted in PBSA buffer). After the incubation, each waveguide was washed once with PBSA, and then incubated with 1 ml of post-coating solution (0.5% bovine serum albumin ("BSA")/0.1% trehalose/PBSA) at room temp. for 1 hour. The post-coating solution was discarded and the waveguides dried in a vacuumed desiccator for an hour.

E. Specific Performance

Figure 21:
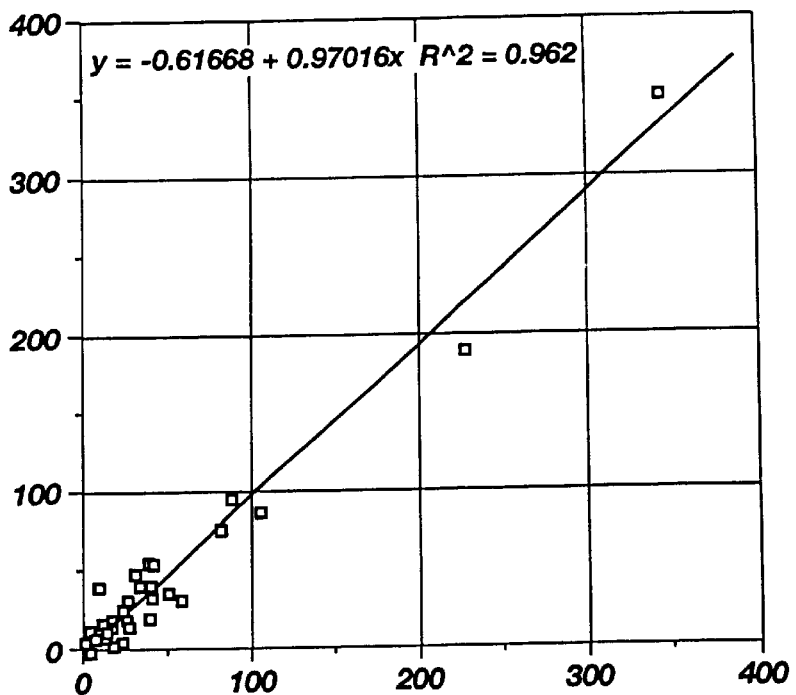
FIG. 21 is a graph depicting the results of a correlational analysis comparing an evanescent assay (CK-MB) of the instant invention with a prior art device.
Figure 22:
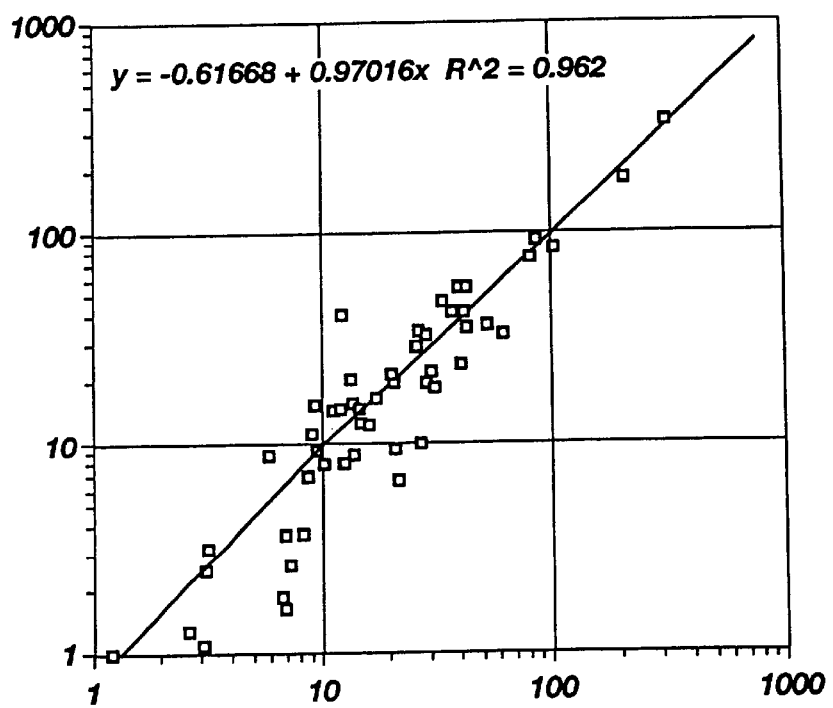
FIG. 22 is a graph depicting the double logarithm plot of the data of the preceding figure showing the correlation.

The correlation of an apparatus according to the instant invention with the ABBOTT IMx assay for an CK-MB assay is graphically depicted in FIGS. 21 & 22. The results showed the two sets of values to be comparable at a correlation coefficient of 0.98, and the sample population contained a higher proportion of samples below 50 ng/ml, the range in which the critical decision point for clinical evaluation has been established in the clinical laboratory environment. FIG. 21 plots the value obtained with the instant invention (y axis, in ng CK-MB/ml) against the ABBOTT IMx value on the x-axis (also ng CK-MB/ml). FIG. 22 depicts the double logarithm plot of the data from FIG. 21 (again, instant invention y-axis, ABBOTT IMx x-axis).

Example X

The preceding example was continued to further establish the utility of the system, and to incorporate more extensive studies of known interfering substances (e.g., hemoglobin and bilirubin), known CK-MB concentrations were analyzed (20 ng/ml CK-MB into human plasma), with concentrations of hemoglobin (15 mg/ml) and bilirubin (1 mg/ml) known to interfere with immunofluourescence assays. The system was still able to detect 100% of the CK-MB.

Characteristics of the described and illustrated embodiments are intended for illustrative purposes, and are not to be considered limiting or restrictive. It is to be understood that various adaptations and modifications may be made by those skilled in the art to the embodiments illustrated herein, without departing from the spirit and scope of the invention, as defined by the following claims thereof.

What is claimed is:

1. A waveguide comprising:
    a planar portion having first and second planar surfaces, a front end and a rear end, and an axis of a plane defined by said first and second planar surfaces, said planar portion capable of transmitting light from said front end to said rear end;
    a front ramp comprising a first associated lens end for receiving light, said front ramp in optical communication with and extending from the front end of said planar portion at a first mean angle other than 0° from the plane; and
    a rear ramp comprising a second associated lens for transmitting light out of said waveguide, said rear ramp in optical communication with and extending from the rear end of said planar portion at a second mean angle less than 90° from the plane;
    wherein light transmitted to the front ramp passes through the planar portion to the rear ramp.

2. the waveguide of claim 1, wherein capture molecules are associated with the first planar surface of the planar portion.

3. The waveguide of claim 1, wherein the waveguide comprises an optical plastic.

4. The waveguide of claim 1, wherein the first angle is a mean angle of from about 15° to 32°.

5. The waveguide of claim 3, wherein the planar portion is composed entirely of an optical plastic.

6. The waveguide of claim 1, wherein the waveguide is integrally formed of optical plastic.

7. A biosensor for use in an apparatus which uses light to analyze a biological liquid, said biosensor comprising:

a waveguide having at least one planar surface and being optically associated with a taper extending therefrom for reading light passing through the waveguide in order to monitor coupling efficiency and beam quality, said waveguide further associated in liquid tight attachment with a first member, said first member, in conjunction with the waveguide, defining at least one reservoir for containing the biological liquid while a planar surface of the waveguide defines a floor or ceiling of said at least one reservoir, the planar surface being associated at least in part with capture molecules, and an inlet and an outlet in fluid communication with said at least one reservoir for infusing and draining said biological liquid into said at least one reservoir so as to allow the biological liquid to contact said capture molecules for interaction therewith.

8. The biosensor of claim 7, wherein a plurality of members sandwiching said waveguide, and at least one of the members sandwiching said waveguide has apertures formed therein thus defining walls of the at least one reservoir.

9. A biosensor for use in an apparatus for analyzing a biological liquid, the biosensor comprising:

a waveguide having at least one planar surface;

a first member in liquid tight attachment with said waveguide, said first member comprising a polymer and defining walls of at least one reservoir for containing the biological liquid and a planar surface of the waveguide defines a floor of said at least one reservoir, the floor being associated in part with capture molecules, the reservoir walls formed of an inert, opaque material.

10. A waveguide comprising:

a front ramp with associated lens end for receiving light, a rear taper for transmitting light out of said waveguide, and a planar portion having first and second parallel planar surfaces for transmitting light from the front ramp to the rear taper so as to transmit light received at the lens associated with the front ramp through the lens associated with the front ramp through the lense associated with the rear taper.

11. The waveguide of claim 10, wherein capture molecules are associated with the first planar surface of the planar portion.

12. The waveguide of claim 10, wherein the waveguide is made from an optical plastic, and the front ramp is angled away from the planar portion's plane at a mean angle of from about 15° to 32°.

13. A biosensor of the type for use in an apparatus for analyzing a biological liquid, said biosensor comprising:

a waveguide having at least one planar surface and at least one tapered surface with respect to said at least one planar surface, said waveguide further associated in liquid tight attachment with a first member, said first member, in conjunction with the waveguide, defining at least one reservoir for containing the biological liquid while a planar surface of the waveguide defines a floor or ceiling of said reservoir, the planar surface being associated in part with capture molecules, and an inlet and outlet in fluid communication with said reservoir for infusing said biological liquid into said reservoir so as to allow the biological liquid to contact said capture molecules.

14. An apparatus for analyzing a biological liquid, said apparatus comprising:

a light source;

a biosensor comprising:

a waveguide having at least on planar surface, and being further associated in liquid tight attachment with a first member, said first member, in conjunction with the waveguide, defining at least one reservoir for containing the biological liquid, the at least one planar surface being associated in part with capture molecules, and an inlet and outlet in fluid communication with said reservoir for infusing and draining said biological liquid into and out of said reservoir so as to allow the biological liquid to contact said capture molecules; and a light detector for detecting light emitted through said at least one planar surface in a direction substantially orthogonal to said at least one planar surface;

wherein said biosensor is oriented in such a way that the at least one planar surface is generally horizontal and level with a surface upon which the apparatus sits so that the at least one planar surface forms a ceiling to said reservoir.

15. An apparatus for analyzing a biological liquid, said apparatus comprising:

a light source;

a biosensor comprising:

a waveguide having at least one planar surface, further associated in liquid tight attachment with a first member, said first member, in conjunction with the waveguide, defining at least one reservoir for containing the biological liquid, the at least one planar surface being associated at least in part with capture molecules, and an inlet in fluid communication with each said at least one reservoir for infusing the biological liquid into said reservoir so as to allow the biological liquid to contact said capture molecules; and a light detector for detecting light emitted through said at least one planar surface in a direction substantially orthogonal to said at least one planar surface;

wherein said biosensor is oriented in such a way that the at least one planar surface is generally horizontal and level with a surface upon which the apparatus sits so that the at least one planar surface forms a ceiling or floor to said reservoir.

* * * * *